US012763194B2

(12) United States Patent
Sperry et al.

(10) Patent No.: US 12,763,194 B2
(45) **Date of Patent: *Oct. 13, 2026**

(54) PATHOGEN DETECTION AND DISPLAY SYSTEM

(71) Applicant: Cardeya Corporation, Naperville, IL (US)

(72) Inventors: Charles R. Sperry, Florence, MA (US); Lawrence J. Pillote, Naperville, IL (US); Vincent A. Piucci, Oakham, MA (US); Dennis F. McNamara, Jr., Walpole, NH (US); James M. Wilson, III, Northhampton, MA (US); Lisa Ruth Stowe, Florence, MA (US); Brett M. Sitzlar, Uniontown, OH (US); Barbara A Piucci, Oakham, MA (US); David C. Chase, Haydenville, MA (US)

(73) Assignee: Cardeya Corporation, Naperville, IL (US)

( * ) Notice: Subject to any disclaimer, the term of this patent is extended or adjusted under 35 U.S.C. 154(b) by 47 days.

This patent is subject to a terminal disclaimer.

(21) Appl. No.: 18/542,130

(22) Filed: Dec. 15, 2023

(65) Prior Publication Data

US 2024/0127943 A1 Apr. 18, 2024

Related U.S. Application Data

(63) Continuation of application No. 16/922,723, filed on Jul. 7, 2020, now Pat. No. 11,862,329, which is a (Continued)

(51) Int. Cl.

*G16H 40/20* (2018.01)
*C12Q 1/04* (2006.01)

(Continued)

(52) U.S. Cl.

CPC ............... *G16H 40/20* (2018.01); *C12Q 1/04* (2013.01); *G06F 3/14* (2013.01); *G06F 3/147* (2013.01); *G16H 50/80* (2018.01)

(58) Field of Classification Search

CPC .......... G16H 40/20; G16H 50/80; C12Q 1/04; G06F 3/14; G06F 3/147

See application file for complete search history.

(56) References Cited

U.S. PATENT DOCUMENTS 5,542,781 A * 8/1996 Yemington ........... E02F 9/2045 37/414
2007/0219645 A1* 9/2007 Thomas ................. G05B 15/02 700/29

(Continued)

FOREIGN PATENT DOCUMENTS

WO WO-2012166812 A2 * 12/2012 ............. G06Q 10/06

OTHER PUBLICATIONS

Lane-deGraaf et al., A test of agent-based models as a tool for predicting patterns of pathogen transmission in complex landscapes, 2013, BMC Ecology, pp. 1-13. (Year: 2013).*

(Continued)

*Primary Examiner* — Christopher L Gilligan
(74) *Attorney, Agent, or Firm* — Duquette Law Group

(57) ABSTRACT

A pathogen detection and display system is configured to discover and display the location of substances of interest, particularly pathogens that can spread infection. The detection and display system can be used in healthcare facilities on surfaces, medical equipment and devices, patients, and staff, for example.

16 Claims, 21 Drawing Sheets

Related U.S. Application Data continuation of application No. 15/133,700, filed on Apr. 20, 2016, now Pat. No. 10,741,278.

(60) Provisional application No. 62/149,912, filed on Apr. 20, 2015.

(51) Int. Cl.

| | |
|---|---|
| ***G06F 3/14*** | (2006.01) |
| ***G06F 3/147*** | (2006.01) |
| ***G16H 50/80*** | (2018.01) |

(56) References Cited

U.S. PATENT DOCUMENTS

| | | | | |
|---|---|---|---|---|
| 2009/0219131 | A1* | 9/2009 | Barnett | G08B 21/245 340/5.2 |
| 2012/0231492 | A1* | 9/2012 | Bitterly | A61B 5/14546 435/287.1 |
| 2013/0120142 | A1* | 5/2013 | Wildman | G08B 21/02 340/539.13 |
| 2013/0318027 | A1* | 11/2013 | Almogy | G16H 50/20 706/52 |
| 2014/0046722 | A1* | 2/2014 | Rosenbloom | G06Q 10/06 702/19 |
| 2014/0167917 | A2* | 6/2014 | Wallace | G16H 40/67 340/10.1 |
| 2014/0244298 | A1* | 8/2014 | Robinson | G16H 40/20 705/3 |
| 2015/0234981 | A1* | 8/2015 | Naidich | G16B 35/00 702/19 |
| 2015/0258228 | A1* | 9/2015 | Cohen | G06F 3/0416 250/492.1 |

OTHER PUBLICATIONS

Read et al., Dynamic social networks and the implications for the spread of infectious disease, Mar. 4, 2008, Journal of the Royal Society Interface, pp. 1001-1007. (Year: 2008).*

Chowell et al., Modeling rapidly disseminating infectious disease during mass gatherings, 2012, BioMed Central, pp. 1-12. (Year: 2012).*

King et al., Modeling environmental contamination in hospital single- and four-bedrooms, Jan. 15, 2015, Indoor Air, pp. 694-707. (Year: 2015).*

* cited by examiner

800

900

PATHOGEN DETECTION AND DISPLAY SYSTEM

RELATED APPLICATIONS

This patent application is a continuation of U.S. Utility application Ser. No. 16/922,723, filed on Jul. 7, 2020, entitled "Pathogen Detection and Display System," which is a continuation of U.S. Utility application Ser. No. 15/133,700, filed on Apr. 20, 2016, entitled "Pathogen Detection and Display System," now U.S. Pat. No. 10,741,278, which claims the benefit of U.S. Provisional Application No. 62/149,912, filed on Apr. 20, 2015, entitled, "Pathogen Detection and Display System," the contents and teachings of each of which are hereby incorporated by reference in their entirety.

BACKGROUND

Each year in the United States alone, 1.7 million patients contract a nosocomial, or hospital-acquired infection (HAI). Ninety-nine thousand people die annually as a result of these infections, making this the fourth leading cause of death in the United States. The direct medical impact of HAIs on the healthcare system is estimated at $35-$45 billion. It is estimated that the combined direct and indirect costs; i.e. impact on humanity, is $96-$147 billion.

An HAI is an infection acquired in hospital by a patient who was admitted for a reason other than that infection. There are numerous varieties of pathogens that can result in HAIs, some of which are antibiotic resistant. The most commonly reported pathogen (as high as 30%) is *Clostridium difficile* (C.diff.), which is also one of the most difficult to remediate. Other pathogens can include *Acinetobacter*, MRSA, VRE, and Norovirus, for example.

HAIs and their treatment are a complicated problem, and for many years have been considered an unavoidable risk and expense. Additionally, the federal Centers for Medicare Services has deemed that certain infections are avoidable, and the care associated with them ineligible for reimbursement. Private payers are following Medicare's lead and beginning to deny payments for HAIs. This trend will certainly continue. Since the Affordable Care Act was enacted in 2010, there have been several changes to the policies regarding reimbursement of HAI costs. The financial burden associated with HAIs is being shifted to healthcare institutions. Beginning in 2015, the 25% of hospitals with the highest rates of HAIs will face penalties of one percent of their Medicare payments.

An additional burden incurred by hospitals as a result of HAIs is an increased length of stay (LOS). Reimbursements from payers to hospitals are treatment-based and independent of the length of stay, so there is a clear benefit to keeping LOS to a minimum. For a patient contracting an HAI, LOS increases from an average of 3.6 days to 22.2 days, with the hospital absorbing the additional costs.

More than ever, the pervasive HAI problem within the healthcare system affects the reputations of hospitals and healthcare providers. The Affordable Care Act of 2010 has established new reporting mechanisms that create online resources where the public can compare the incidence of HAIs at their local hospitals. Clinical care outcomes will become visible to patients, allowing them to become more selective about their care providers in ways that will have a significant effect on a hospital's overall patient volume and bottom line.

SUMMARY

Recent academic and clinical research has begun to demonstrate that infections can be dramatically reduced through proper disinfection of the hospital environment. However, it is hard to clean what cannot be seen. The cleaning, disinfecting and sanitizing of surfaces in facilities that service the public happens continually. Every minute of each day wait staff in restaurants wipe down tables with diluted bleach spray, janitors clean public restroom floors with a rolling bucket and mop, and hospital housekeeping staff disinfect patient rooms with a spray bottle and wipe rag then move on to the next room. There are no standards for cleaning. Since there is no method to visualize pathogens, the cleaning products and methods used are based on tradition and common knowledge rather than on scientific evidence.

These efforts are carried out with a host of cleaning products to remove dirt and debris, and chemical disinfecting and sanitizing products are used to kill bacteria, spores and viruses. Technologies utilizing ultra-violet light, dry fog, ozone, hydrogen peroxide gas and other media are employed to sanitize hospital rooms. With all this effort, technology, manpower and regulation, the spread of infection from pathogens left on cleaned surfaces is still commonplace, with costly, debilitating and even deadly results for the humans who come into contact with the surfaces.

An inherent problem with the current methods of monitoring, cleaning and disinfecting is that pathogens cannot be seen with the naked eye. The cleaning staff is literally blind in the environment that they are charged with cleaning. Thorough disinfection of hospital rooms is a key component of preventing infections. Numerous chemicals and methods are available that have the ability to kill pathogens. However, infectious pathogens are microscopic and difficult to detect and identify. Because of this, pathogens are often left behind after the cleaning and disinfecting process, and have the ability to infect a subsequent patient.

Current methods to monitor and verify cleaning activities are limited. For instance, in some hospitals a method using fluorescent dots and UV light is used to verify that a surface has been cleaned. The dots are placed in high-touch locations that are unknown to the cleaning staff. The rooms are then cleaned, and then the locations are checked to determine whether the dots have been removed. This practice verifies that the dye has been removed, but provides no information about the presence of harmful pathogens.

Photoluminescence is used to test for the presence of adenosine triphosphate (ATP). Wherever organic biomass is found, ATP will be present. This test helps to indicate that a surface has been cleaned, but, as with fluorescent dye, does not detect the presence of harmful pathogens. While tests such as these are a step in the right direction, it still leaves the staff blind as to what needs to be cleaned and the efficacy of cleaning techniques.

There are methods available that can identify a pathogen. The most common involves taking a sample from a surface and culturing it in a growth medium. Others include DNA testing, chromatography/spectroscopy, and an emerging technology using disposable biochips. Depending on the type of test used, definitive results can take up to 48 hours. Without a methodical sampling procedure and a method to display results, these are limited to use as spot sampling techniques.

Conventional methods attempt to predict trends and even length of stay related to HAIs. These methods are generally based on data mining and retrospective analysis, although some also include patient and location testing. Results are used to predict trends over time, but none of these can, or are intended to, show the current locations of pathogens.

Other conventional systems include cleaning validation systems which are used to help assure that particular cleaning procedures have been followed. These systems often include means to verify that disinfectants have been used, staff has cleaned their hands, etc. Some prior art mentions the use of pathogen culturing to validate cleaning. The disadvantage to relying on validation is that a patient, visitor or staff member may enter the space and touch a surface immediately after validation, depositing a pathogen onto the surface, and contaminating the validated room. This can result in a false confidence of room cleanliness.

Clearly, hospitals need better strategies for preventing HAIs. Embodiments of the innovation disclosed herein provide hospital staff with the ability to obtain a picture of the presence and locations of pathogens within the facility. With this information, pathogens can be remediated and HAIs will be reduced. The prevention of HAIs will become an evidence-based practice rather than one that depends on traditional methods that are scientifically unsupported.

By contrast to conventional cleaning methodologies, embodiments of the present innovation relate to a pathogen detection and display system. In one arrangement, the pathogen detection and display system is configured to discover and display the location of substances of interest, particularly pathogens, which can spread infection. Pathogens include organisms, such as an infectious particle capable of producing a disease, that cause disease or illness to its host or any substance of interest that can cause illness, irritation, etc. Embodiments of the innovation can be used in healthcare facilities on surfaces, medical equipment and devices, patients, staff, etc. It can also be used in restaurants, on cruise ships, in theaters, prisons or any other space where the spread of pathogens can cause harm. This disclosure will describe a system for use within a health care environment, but it will be seen that it can be employed in other applications as well.

Hospital staff is challenged with chasing invisible and deadly pathogens through the environment without clear feedback about which remediation efforts work and which do not. Despite their best efforts, they have no way to confirm which actions are effective in reducing HAIs. With this disconnect, hospitals have adopted a "bundled approach" to intervention. This approach includes written policies and procedures, education of staff, selection of cleaners and disinfectants, methods of cleaning, and monitoring of cleaning practices. Without data, there is merely a loose coupling of remediation activities and efficacy. Ultimately, there is no clear proof which bundles are truly effective for reducing HAIs. Additionally, there are no standards for cleaning within a healthcare facility, which means that each facility, unit and even cleaning crew may use different techniques.

This innovation is an integral part of an evidence-based practice (EBP) that can significantly reduce the occurrence of HAIs. Disclosed is a scientific auditing system as opposed to a verification or validation system. The process of continually auditing a facility and displaying the location of pathogens precludes the need for verification of cleaning since it creates the opportunity to adapt behaviors and protocols based on scientific evidence.

EBP is the integration of scientific evidence, clinical expertise and client/patient perspectives. The current innovation contributes the scientific evidence to the practice. With knowledge of the location of pathogens within a facility, clinical expertise can be employed to determine methods and protocols that best remediate and prevent pathogens. With the continuing auditing cycle, the efficacy of the methods and protocols will become evident. This continuing scientific evidence will allow clinicians to modify or select the remediation and prevention methods and protocols that are most effective. Decisions will no longer be based on opinion and ungrounded tradition but on visible, demonstrable evidence. This system will provide the health care facility with the necessary tools to determine best practices.

In its basic embodiment, this innovation is a three part system:

Collect; healthcare or environmental services staff collect samples from rooms and locations within those rooms as instructed by the system.

Read; the sample results are read to identify potentially harmful pathogens and their locations.

Display; the presence and location of pathogens are displayed in a manner that provides a visual representation of their location.

In one embodiment, the system automatically analyzes the collected samples, formats the results as needed, then displays individually tailored information to front line staff, infection control, hospital administration, admissions, housekeeping and other departments and individuals as needed. The display of information can be via tablet, smart phone, computer, wall-mounted video monitor, existing facility communications systems or other convenient means.

In certain embodiments, the system is configured as an adaptive, self-learning system that utilizes the continuing feedback to maximize its ability to detect pathogens. It can adapt collecting techniques to particular facilities or types of facilities, location within a facility, and type of room or even specific rooms and location within rooms. It may take into account the pathogen types and their traits, such as the locations where they are commonly found, for example. The substantially continuous feedback cycle provides this adaptive system with the information it needs to determine the most effective sampling protocols based on factors that can include type of pathogen, location of pathogen, size of colony and various historical data; then uses the data to adapt sampling methods and locations based upon quantifiable results. Some embodiments may use these adaptive learning methods to direct cleaning and remediation efforts by providing specific instruction based on the type of pathogen found, its location, etc.

In one arrangement, a pathogen detection and display system, comprises a collection device configured to retrieve a sample from a facility, a reading device configured to receive the sample from the collection device, to process the sample, and to generate pathogen sample information related to the sample, a control system disposed in electrical communication with the reading device, and a display device disposed in electrical communication with the control system. The control system is configured to receive, from the reading device, primary pathogen sample information related to a pathogen associated with a facility. The control system is configured to correlate the primary pathogen sample information with a pathogen transmission factor, the pathogen transmission factor associated with transmission of the pathogen within the facility. The control system is configured to, based upon the correlation of the primary pathogen sample information and the pathogen transmission factor, transmit pathogen action information associated with the primary pathogen sample information to the display device.

BRIEF DESCRIPTION OF THE DRAWINGS

The foregoing and other objects, features and advantages will be apparent from the following description of particular embodiments of the innovation, as illustrated in the accompanying drawings in which like reference characters refer to the same parts throughout the different views. The drawings are not necessarily to scale, emphasis instead being placed upon illustrating the principles of various embodiments of the innovation.

DETAILED DESCRIPTION

Embodiments of the present innovation relate to a pathogen detection and display system. In one arrangement, the pathogen detection and display system is configured to discover and display the location of substances of interest, particularly pathogens that can spread infection. Embodiments of the innovation can be used in healthcare facilities on surfaces, medical equipment and devices, patients, and staff, for example. It can also be used in restaurants, on cruise ships, in theaters, prisons or any other space where the spread of pathogens can cause harm.

Figure 1A:
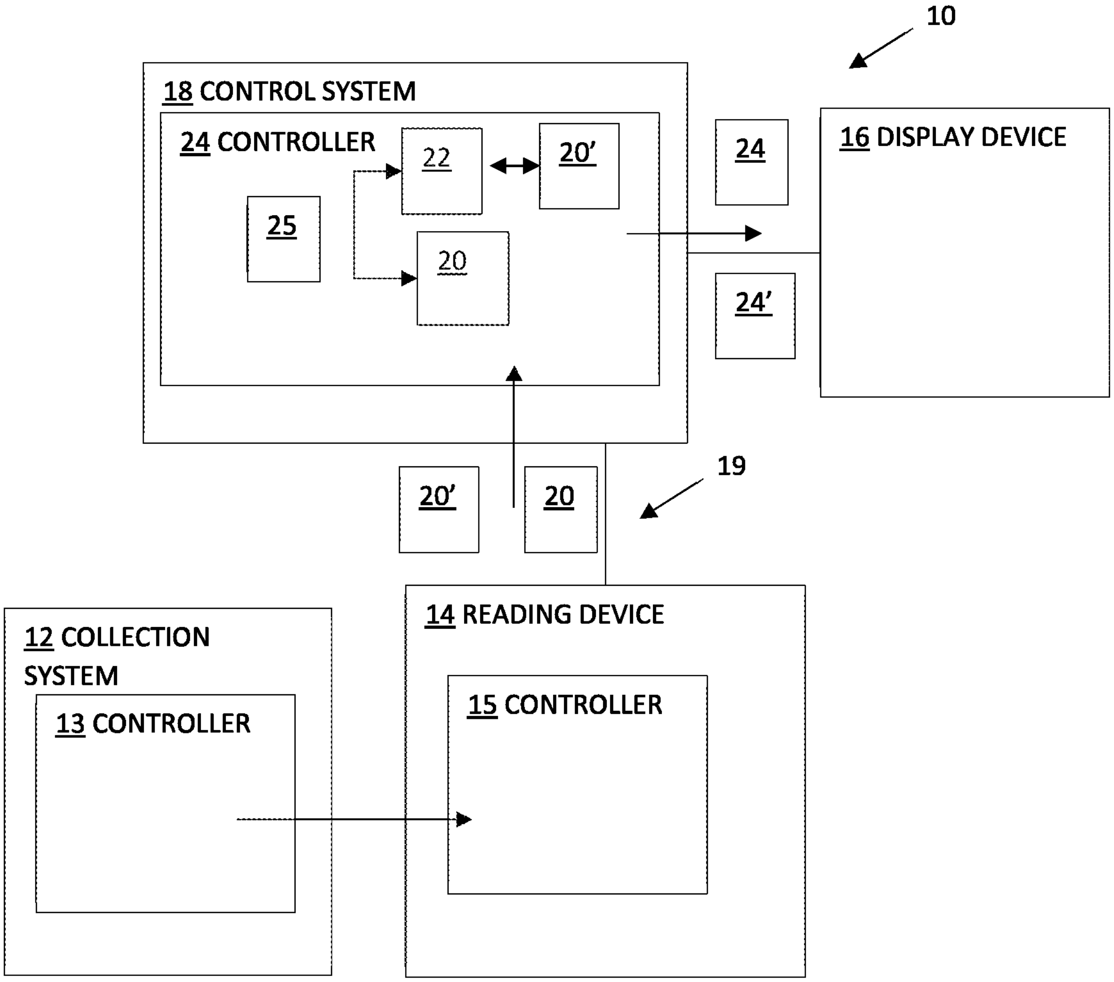
FIG. 1A illustrates a schematic representation of a detection and display system, according to one arrangement.

FIG. 1A illustrates a schematic representation of a detection and display system 10, according to one arrangement. As shown, the system includes a collection device 12, a reading device 14, a display device 16 and a control system or controller device 18.

The collection device 12 is configured to retrieve samples from a facility or worksite for the testing of pathogens. For example, the collection device 12 can be a computerized device having a controller 13, such as a memory and a processor. One arrangement of the collection device 12 is illustrated and described with respect to FIGS. 12-16 below. Returning to FIG. 1A, the collection device 12 is disposed in operative communication with the reading device 14. For example, the collection device 12 is configured to provide the collected (e.g., physical) samples to the reading device 14 for processing.

Figure 18:
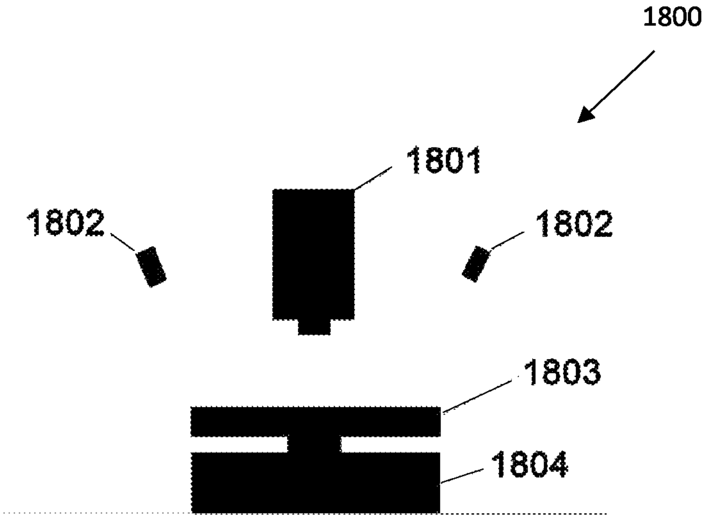
FIG. 18 illustrates a schematic representation of the components within a reader system, according to one arrangement.

The reading device or system 14 is configured to receive the collected samples and processes the samples to determine whether a pathogen is present. For example, with reference to FIG. 1A, the reading device 14 can be a computerized device having controller 15 such as a memory and a processor. One arrangement of the reading device 14 is illustrated in FIG. 18 below. Returning to FIG. 1A, the collection device 12 is disposed in electrical communication with the control system 18. For example, the reading device 14 is configured to communicate with the control system 18 via a wired or wireless network 19, such as a LAN or a WAN. During operation, the reading device 18 is configured to transmit pathogen information 20, which relates to a detected pathogen, to the control system 14.

The control system 18, such as a computerized device having controller 21 such as a memory and a processor, is configured to utilize the pathogen information 20 to provide information, such as pathogen action information 24, regarding the detected pathogen, such as via display device 16, to an end user. An example of the operation of the control system 18 is provided in detail below.

Figure 1B:
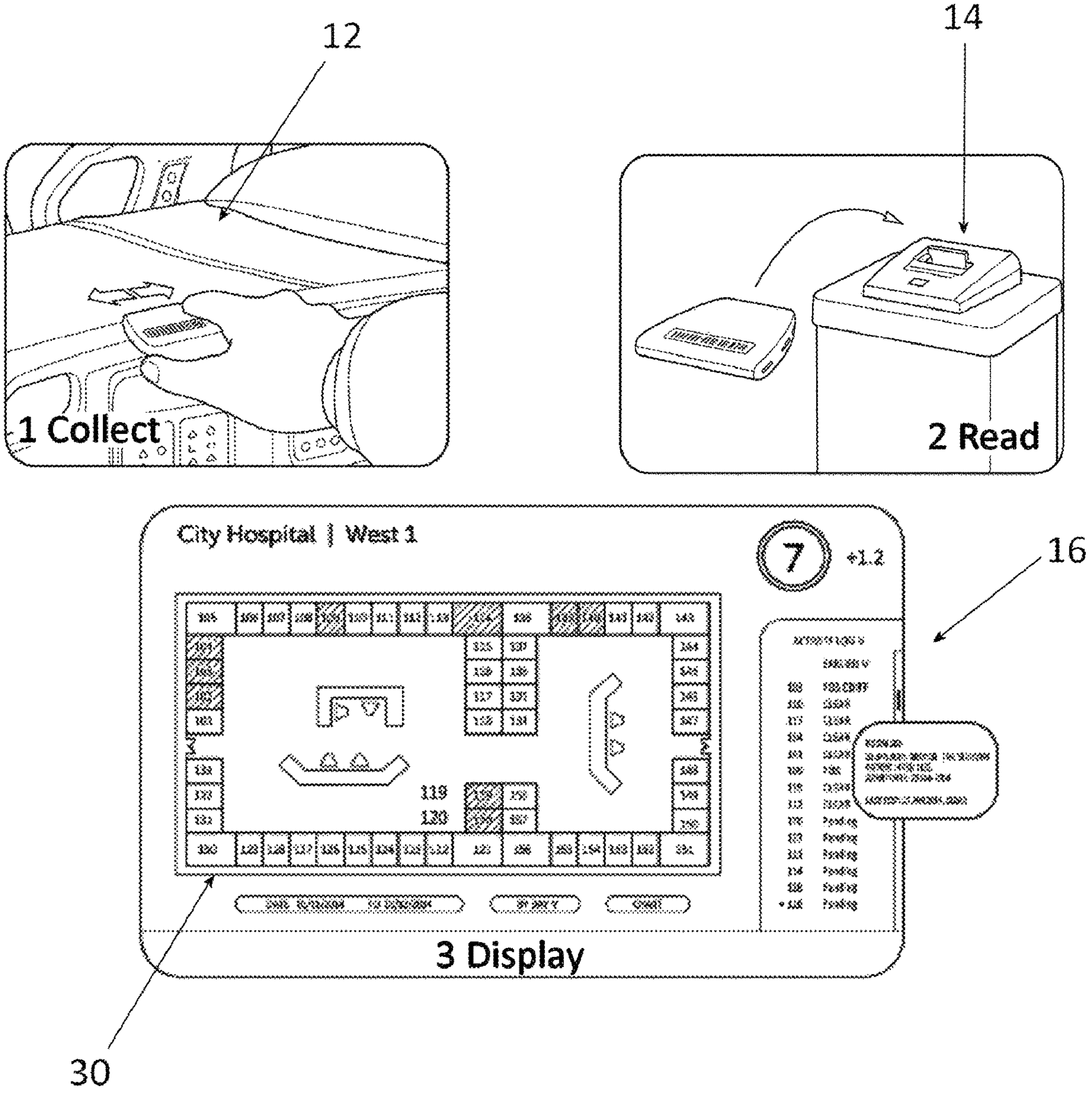
FIG. 1B illustrates an example of a detection and display system, according to one arrangement.

FIG. 1B illustrates an example of the collect-read-display functions of a pathogen detection and display system 10, such as illustrated in FIG. 1A, according to one arrangement. The collection and reading devices 12, 14 and display 16 shown here are functional examples only. These elements 12, 14, 16 and their functions may take many alternative forms depending upon the specific applications and technologies used. Examples of the three functions of the system 10 are provided as follows:

Collection Functionality

In one arrangement, the collection device 12 is configured to take samples to test for pathogens. These are generally taken from surfaces within a hospital, and can include a room's walls, floor, windows, etc., as well as beds and other furnishings, medical devices and equipment. Samples may be collected from patients, caregivers, visitors or from any other entity that may provide usable information to the system. Collection technicians may be nursing or environmental staff, or other personnel trained in the process, who may be hospital employees or staff supplied by an outside company. The collection device 12 provides the staff members with instructions that include all the information necessary for collection. Instructions may include the time when a collection is to be taken, the specific location or locations to sample, the type of sample to take (i.e. there may be different collection devices for different pathogens of interest), disposition of collected sample and any other relevant information.

Reading Functionality

In one arrangement, the reading device 14 accepts the collected samples and processes them to determine whether a pathogen is present. The determination may be as basic as pathogen or no pathogen, or may include specific pathogen family, genus, species, colony count, biomass or other pertinent information. In one arrangement, the pathogen information determined here is provided to the display device 16 via the control system 18. In one embodiment, the reading device 14 is automated and configured to have the technician insert the collection device 12 into the reading device 14. However, a completely manual system is within the scope of this innovation. For example, manual culturing and identification can be provided by a morphologist, or by DNA or other high-tech methods. Alternately, an automated system, such as described below, can be utilized Displaying Functionality In one arrangement, the display device 16 presents pathogen information determined by the collect and read functions to the personnel responsible for hygiene, infection control and management of the facility. The display method and format can be tailored to the target user to provide them with the most appropriate information in an easy to use fashion. The display output example in FIG. 1B may be well suited for use by infection control and cleaning staff. It depicts a floor map of a hospital outlining individual rooms. The highlighted rooms are contaminated by pathogens, and the others are not. This display output provides hospital staff with a simple visual understanding of the areas that need immediate attention. A display output meant for a hospital manager may present statistics, reports and analyses rather than a map. Display outputs may be tailored by individual, function or other criteria. The display device 16 may be interactive, allowing the user to select and choose information and presentation format, as preferred. Additionally, the display output may be provided on any suitable display device 16, such as computers, smart phones, tablets, wall-mounted monitors, dedicated devices, existing facility communication systems, etc.

In one arrangement, the system 10 includes a control system. In one embodiment, the system 10 is configured as a cloud-based system, such as having a server device, which can support one or multiple facilities. For example, using a secure internet connection, cellular or other suitable communication technology, results from the reader device 14 are transmitted to the control system 18 having a controller 21, such as a memory and a processor, configured to process the results and to transmit the processed results to one or more display devices 16. Alternatively, the control system 18 can utilize a facility's mainframe computer, a device with an embedded system, a PC-based computer or other suitable technology. In one embodiment, the system 18 informs hospital staff of the location of pathogens. In one arrangement, it is the responsibility of the staff to determine the proper course of action to remedy the situation. This system 18 provides the scientific evidence, such as typically required for an evidence-based practice. The staffs clinical expertise is used to remediate the problems and to understand the ramifications of their choices based on ongoing pathogen auditing results. This provides the staff with the ability to see the location of pathogens and to realize the efficacy of their protocols. The comparative effectiveness of protocols will become apparent over time. This will provide the opportunity to maximize remediation efficacy and minimize contamination, resulting in fewer HAIs.

Knowledge of the location of pathogens will also give hospital staff the ability to adapt patient treatment. For example, if a particular pathogen is found in a patient's room and the patient is deemed susceptible to it, a course of antibiotics may be started prior to the patient showing symptoms of infection. Other behavioral changes can result from this innovation as well, because for the first time, hospital staff will be able to truly understand the effectiveness and results of their methods, procedures and techniques.

In use, the control system 18 is configured to provide instructions for collecting samples. For example, the control system 18 is configured to provide a trained technician or team of technicians with instructions via smart phone, tablet, existing hospital communication system, or other convenient device. This may be the same display device 16 that is used to display the pathogen location results, or it may be a different device. These instructions may also be delivered by a non-electronic device, such as a paper printout. These instructions include information such as which rooms are to be sampled, the sampling location or multiple locations within that room, the type of sample to be collected if more than one is available, time of day to take the samples, disposition of the sample after it is collected, or any other information that is pertinent to the collection and handling of samples.

The technician then proceeds to collect samples as instructed. In one arrangement, the sample is collected using a collection device 12 that allows relatively rapid collection by touching a collection device 12 to a surface within the room, equipment and devices within the room, or even patients and staff. This collection device 12 may be used to take a single sample, or may be used to sample multiple locations; i.e. bed rail, window sill, etc., as instructed. Each individual collection device 12 is identified and logged into the system. Each collection device 12 can be individually serialized and can be read into the system by use of bar code, RFID tag or any other convenient identification method. Identification may also be made by manually logging a serial number or other identifier into the system. Alternative methods may also be used. For example, individual labels may be printed, whereby the staff member taking the collection places the label onto the collection device 12 at time of collection. This label correlates each collection device 12 with its sampling instruction. Numerous methods can be used by the system 10 to link any sample to its instruction, as well as time of day, etc. In this manner, the pathogen display system 10 can relate each collected sample to its correct location and time.

Once samples are collected by the collection device 12, the samples are provided to the reading device 14. In one embodiment, the reading device is configured to automatically detect the presence of a pathogen based upon the samples. For example, once the collection device 12 is inserted into the reading device 14, the reading device 14 is configured to automatically determine whether a pathogen is present or not. This may be accomplished by a variety of mechanisms, from manual culturing and identification by a morphologist to DNA or other high-tech methods, to the automated system described later. Delivery of the collected samples to the reader may be accomplished in a variety of ways, such as human currier, existing pneumatic delivery systems, robotic delivery devices, etc. The reading device 14 may be localized to a hospital floor or a centralized hospital location, or even a more centralized, regional location outside of the hospital that may serve multiple facilities.

The collect-read-display process can function as well with various reading device models. In one arrangement, if an automatic reading device 14 is not used, a manual system may be employed. For example, a sample may be collected using a currently available swab sampler that is identified as previously described. The sample is then delivered to a laboratory, where it is cultured and grown. A morphologist determines whether a sample contains a pathogen. This information can then be manually entered into the system.

As indicated above, the collection device 12 and reading device 14 are configured as separate devices. Such indication is by way of example only. In one arrangement, the collection and reading devices can be combined into a singular device that consolidates the collect and read function. This singular device would collect and read a sample and send the pathogen information to the control system. A singular device containing collect, read and display functions would also be anticipated by this innovation.

Display

Once the pathogen information is collected and read, the control system 18 provides information, such as pathogen action information 24, to the display device 16. In one embodiment, the pathogen action information 24 is configured as a facility map 30 outputted by the display device 16. The facility map 30 is configured to provide a pathogen sample identifier, such as a type of pathogen identified in the facility, a pathogen sample location, such as a visual representation of the location of pathogens within the facility, and a pathogen sample time. Also as part of the pathogen action information 24, the display device 16 can provide a list of room numbers with an indication of a positive or negative test result, or may provide detailed information about the type of pathogen found, specific location of detected pathogens (bed rail, door knob, blood pressure monitor, etc.), and any other information that may aid in remediation and prevention.

The display example in FIG. 1B depicts a display output that may be used by front-line staff responsible for remediation and patient safety. In this example, a map of the floor plan depicts room locations and identification. Rooms where no pathogens have been found are shown in a first color, such as blue. Rooms that have pathogen contamination are shown in a second color, such as red. This provides the staff with an instant visual recognition of locations that need attention. Other information presented in the FIG. 1B example is the name of the hospital and floor within the hospital, total number of contaminated rooms, and an activity log containing the status of recent audits.

In some embodiments, the display device 16 is configured as an interactive device that can be accessed through a touch screen or other selection method. For example, a staff member may select a room of interest by touching the screen to get detailed information about the testing and results within that room. The example in FIG. 1B depicts a room selected with additional information shown. Through the interactive display, the user may select a variety of informational and visual formats. Examples include multiple levels of detail, historical information, data trends, graphical representations vs. lists, or any other data and presentation that can be helpful to the staff. Following are illustrative examples of the display, its contents and interactivity.

Figure 2:
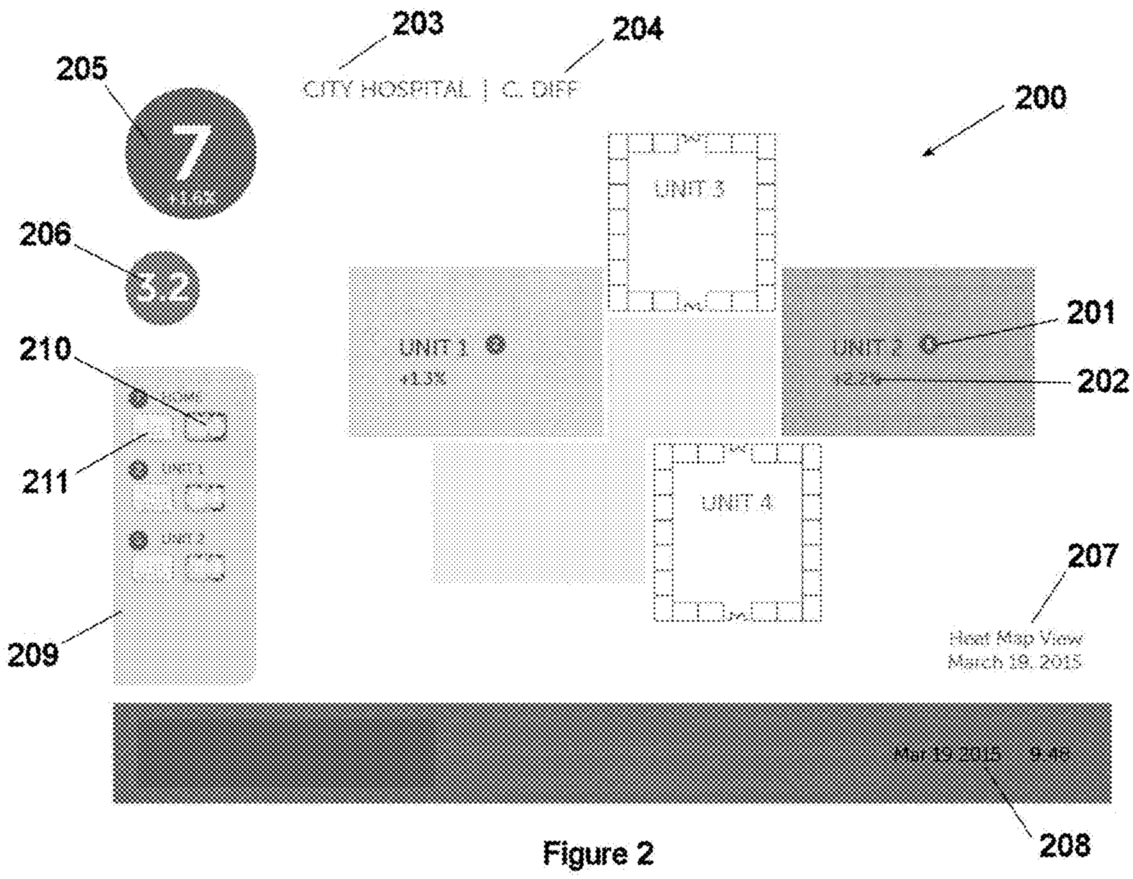
FIG. 2 illustrates an embodiment of a pathogen display screen.

FIG. 2 shows an embodiment of a pathogen display home screen or display output, as provided by display device 16. In it can be seen a plan view of the four units within the hospital 200. Units 1 and 2 are depicted in a first color, such as red, indicating that pathogens have been found in these units. The intensity of the color indicates the relative number of positive pathogen results within that unit. For example, unit 2 is a darker shade than unit 1, meaning more pathogens were found there than in unit 1. Within the unit maps are the total number of positive pathogen results 201, in this case 5 rooms are contaminated. Also displayed is the change in the number of contaminated rooms 202, in this case it has increased 2.2% from the previous reporting period. The reporting period may be the current calendar day, the prior 24 hours, or other period as desired. Units 3 and 4 are shown as unshaded (i.e., in white) meaning that they are not included in the testing. If a unit being tested has no pathogen presence, it can be depicted in a second color, such as green, blue or another color, indicating it is pathogen-free.

Also provided by the display output are the facility name 203 and the pathogen being detected 204. The display output may show the total number of room that have tested positive along with the percentage change for the facility 205, and may display the average patient stay 206, in this case 3.2 days. The display output may also show the map title and information date 207 as well as current date and time 208. A navigation panel 209 allows the user to select the page view for the home screen as well as individual units. The current view is the map view of the home page 210. The display output may include features for ease of navigation. For example, selecting a unit on the screen may bring up the detailed display for that unit. Selecting the chart view 211 brings up an historical graph display of pathogen results.

Figure 3:
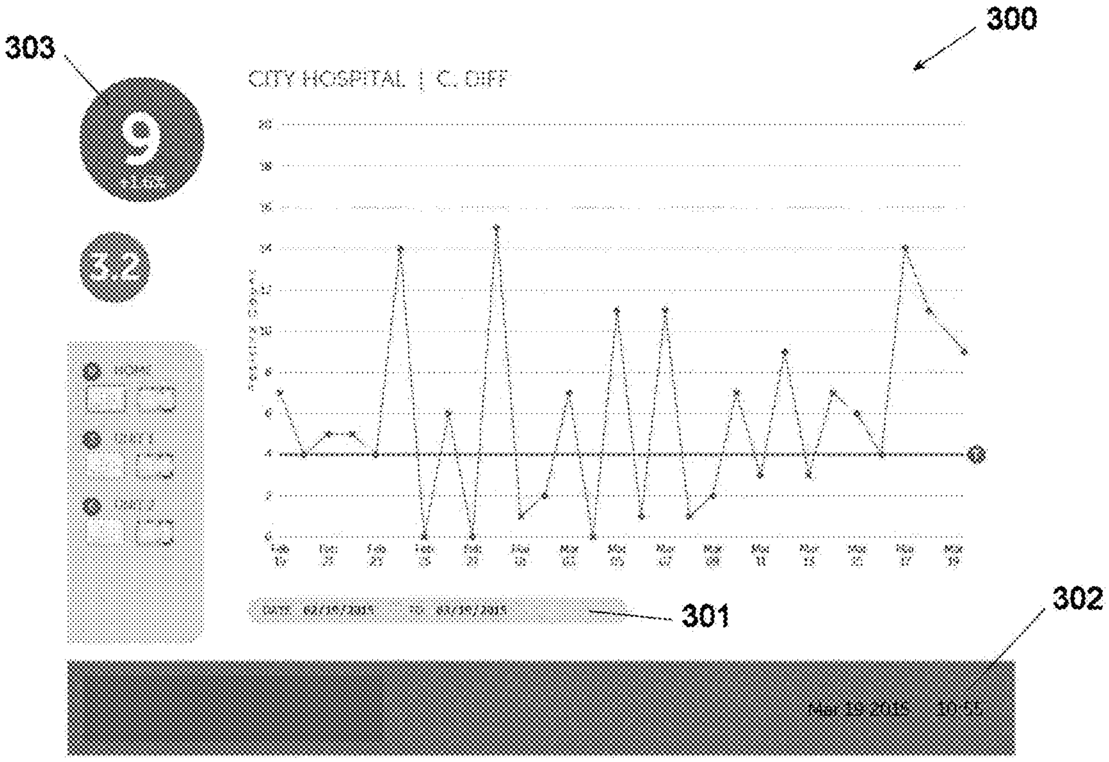
FIG. 3 illustrates a historical graph provided by a display.

The display output can also provide standard statistical calculations such as average, mean, standard dev, or % change, for example. FIG. 3 shows a display output of a historical graph 300. The date range 301 shows that this graph represents the time period of 2/19 to Mar. 19, 2015. The graph 300 depicts the total number of rooms that test positive for each day of the month. As can be seen in this example, during the one hour and seven minute elapsed time between the current date and time 208 of FIG. 2 and current date and time 302 of FIG. 3, the total number of contaminated rooms during the reporting period has risen from 7 to 9 303. This illustrates how the display device 16 functions in real time.

Figure 4:
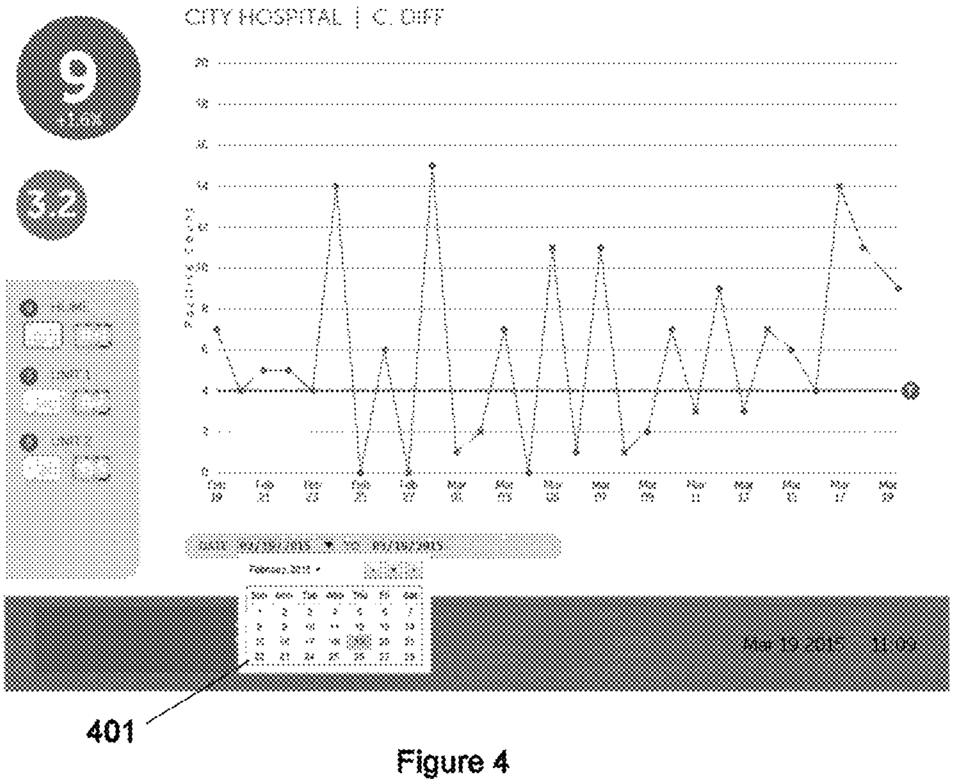
FIG. 4 shows a drop-down menu that can be used to change the historical date range.
Figure 5:
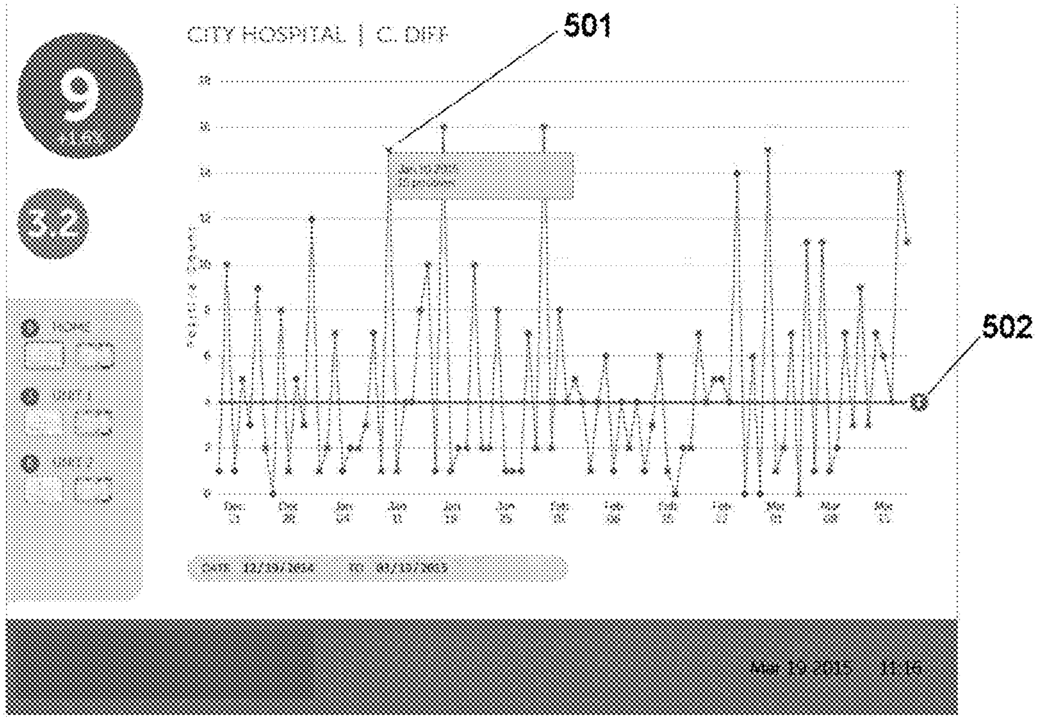
FIG. 5 shows a change in the historical date range to display a prior three months of history.

FIG. 4 shows a drop-down menu 401 that can be used to change the historical date range. For example, a user can select the drop-down menu 40 to change the display from a prior month of history to a prior three month of history. FIG. 5 shows the range changed to display the prior three months of history. Selecting any point 501 on the graph may display information specific to that date. A trend line 502 may be used as an indicator of the level at which action must be taken, in this case, four contaminated rooms. The probability of spreading infection is related to the amount of pathogen present and the number of locations that are contaminated. There may be a number of contaminated locations under which only a limited remediation effort is necessary for the probability to remain low. Anything above this line may require immediate and/or intensive effort to reduce the pathogen content. This number may be decided upon based on historical data and trends, as well as location or other factors. For example, an oncology unit may require a lower contamination tolerance than an outpatient unit since the oncology patients will tend to have compromised immune systems, making them more susceptible to infection. Along with this trend line, the graph may show the average, median, standard deviations or other desired information.

Figure 6:
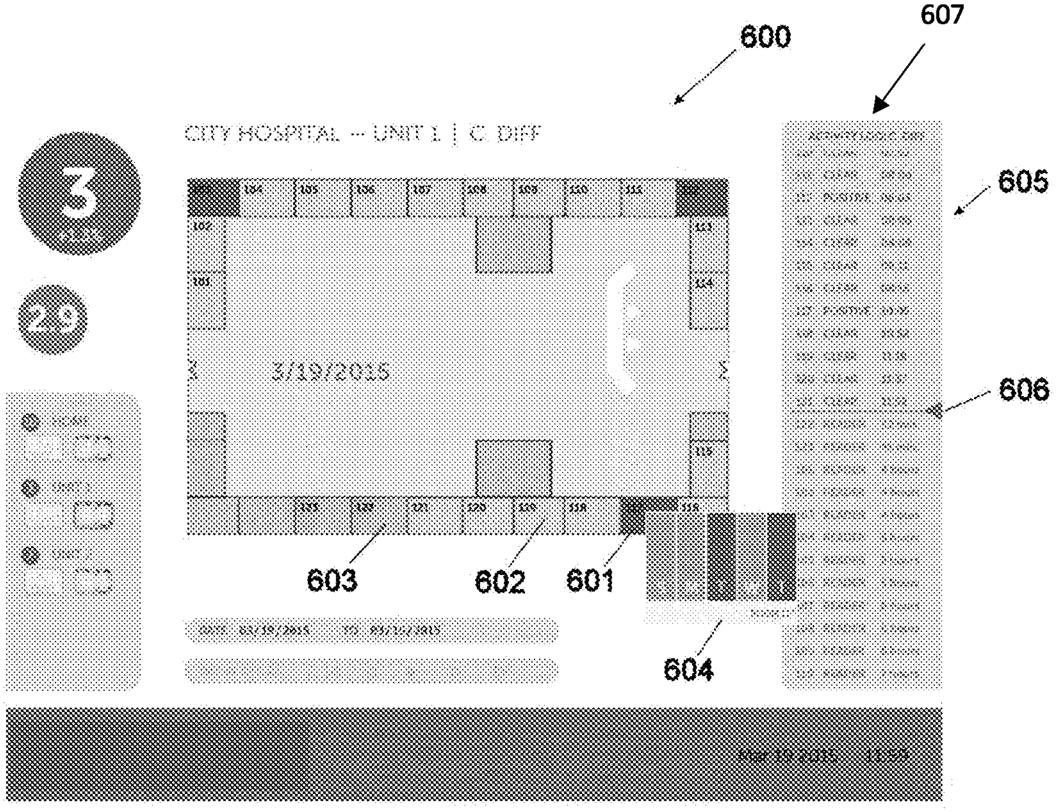
FIG. 6 illustrates a map of Unit 1 showing room locations and room numbers.

FIG. 6 depicts an example display output as a map 600 of Unit 1, showing room locations and room numbers. This is a map 600 of the current reporting period, in this case, 24 hours. As illustrated, any room shown in a first color 601 has tested positive for pathogens in its most recent audit. Rooms shown in a second color 602 did not test positive for pathogens in their most recent audit. Rooms that are half shaded 603 are rooms that have a pending test result. The color of the shaded half indicates the prior day's test result. In this figure, room 117 has been selected, which has brought up a window 604 showing the prior week's results, with each day shaded in a first or second color depending on results.

To the right of the map is provided a status window 605 having status entries 607. Status entries 607 provided above the line 606 are completed tests, while entries provided below the line 606 are pending. The completed test results are displayed in a first or second color to indicate positive or clear (negative) results, and show the room number, result status and time of test. The pending results show the room number, status and the time remaining until results are known. The status in this case is Reader, meaning that samples have been collected and are in the reader awaiting results. Other status entries may include tests that are scheduled, collections being made, in transit between collection and reader, etc. The status line may be selected and dragged upward or downward to view past or future status entries.

Figure 7:
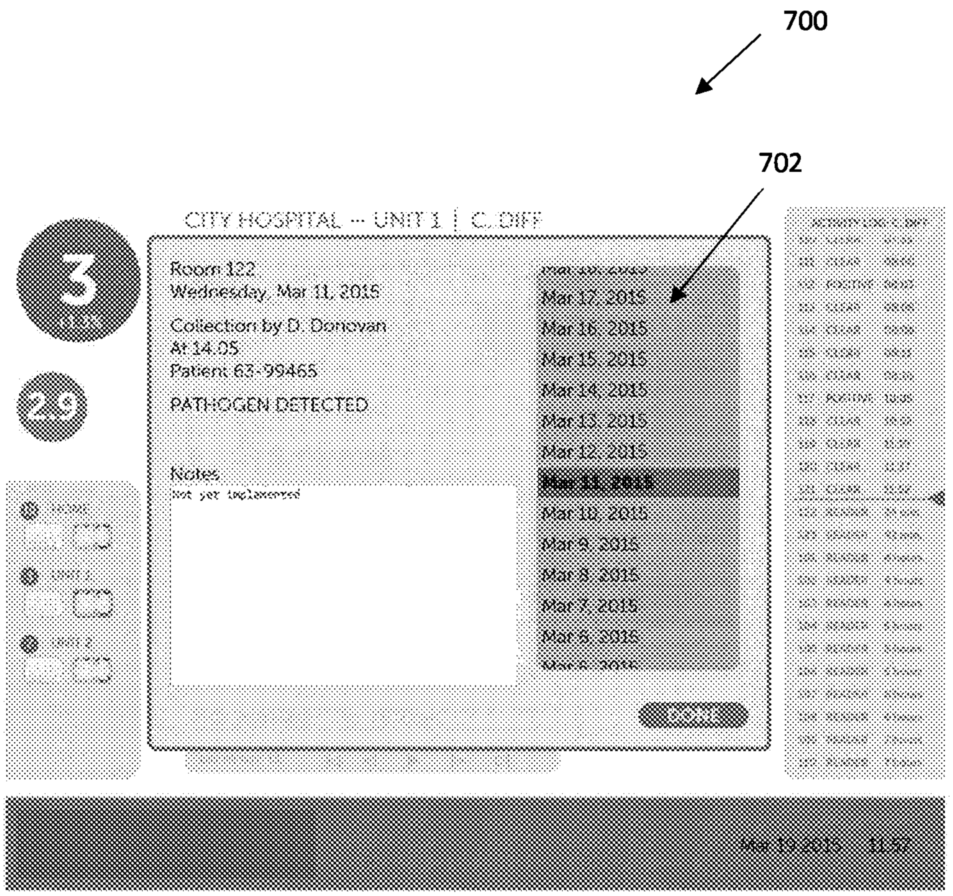
FIG. 7 illustrates a detail window.

User selection of a status entry 607 may bring up a detail window 700 as the display output, as shown in FIG. 7. The window 700 can include detailed information about an individual test result including room number, date of collection, staff member making the collection, the patient in the room, test results, notes, and may even include data about staff on duty or any other relevant information including qualitative and/or quantitative pathogen data.

Figure 8:
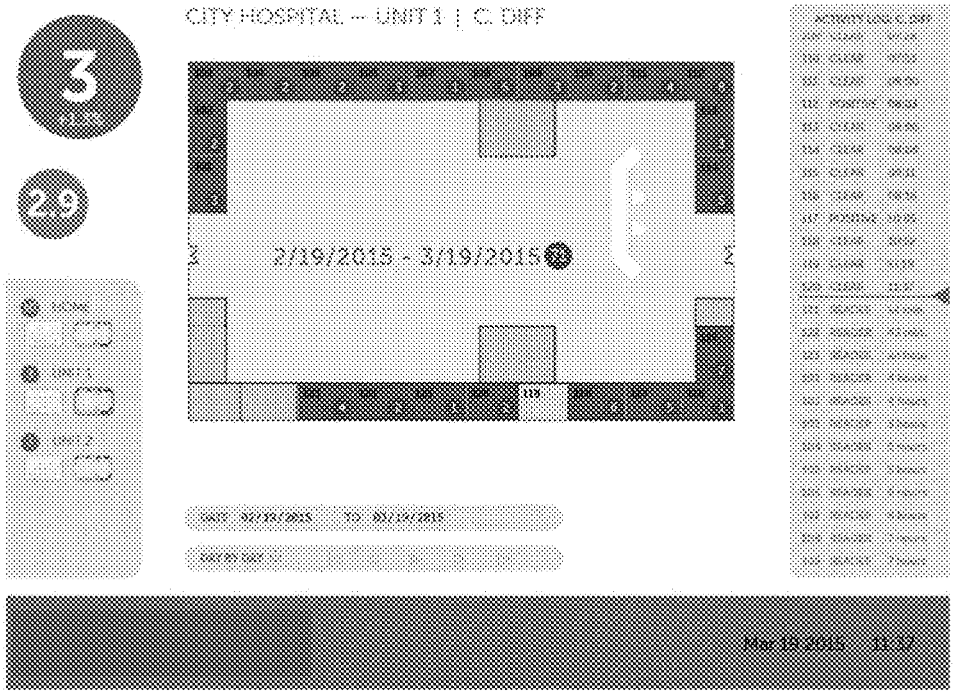
FIG. 8 shows pathogen detection results from a one month period.
Figure 9:
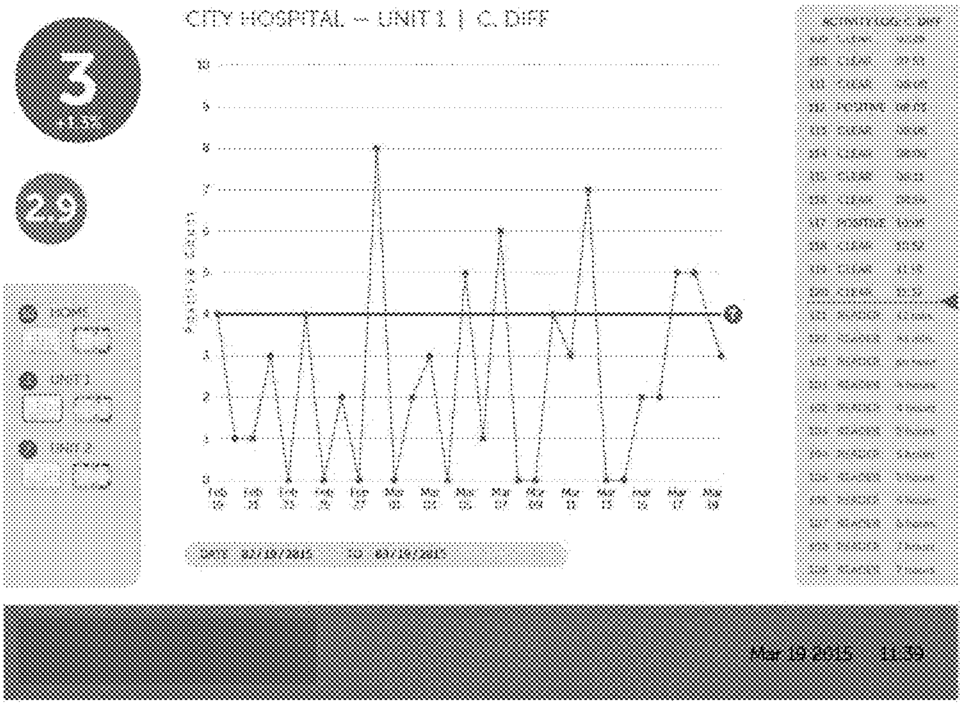
FIG. 9 illustrates unit data provided in graph form.

As with the graph results shown previously, the display dates 702 may be selected by an end user to view historical data. FIG. 8 shows the display output providing results 800 from a one month period. Any rooms that tested positive within this time are shown in a first color, along with the number of days that the test results were positive. This can be displayed as the number of positive results, can be shown as a percentage, or may be a calculated number indicating a persistence factor. A persistence factor may make it possible to recognize rooms that should be investigated because of a persistence or pattern of persistence of pathogens. The persistence factor may be a calculation based on number of recurrences, size of pathogen colonies and other elements that will be determined by practice of the art. Selecting a specific room can bring up a window with that room's historical data. Additionally, the display may be cycled through day by day to view the changing results. As with the whole facility map, the unit data may be viewed in graph form 900 as in FIG. 9.

Although not shown in the Figures, one aspect of the system 10 is the ability to display not only the location and number of occurrences of pathogens, but also quantitative information as well. This may be presented as the percentage of surfaces that are contaminated with pathogens. This may be the percentage of surfaces tested, or an extrapolation of the total contaminated surfaces within an area based on test sample locations and results, and the understanding of pathogen growth and contamination trends learned from historical data. Alternatively, or in addition, the quantitative measure may relate to the size of the pathogen colonies. The size may be the area of an individual colony, expressed in units such as square inches, square centimeters, etc. It may be the volume in cubic inches, cubic centimeter, etc., or it may be the mass of the colony in grams, ounces, etc. The display may present this information in a manner that is most helpful in understanding contamination levels, trends, etc. For example, the charts and graphs shown in the figures that display information about room contamination may include this quantitative information as rough data, percentage of increase or decrease, levels requiring immediate attention, etc.

In one arrangement, the data and presentation can be user dependent. For example, an infection control officer may view a hospital-wide contamination map. A historical map can identify locations of recurring pathogens, indicating problem areas that need investigation. A hospital administrator can obtain analytical information, comparisons, and reports. An admissions department may use the information to place incoming patients with a known susceptibility into rooms with historically low pathogen content. As can be seen, the system allows all users of the system to visualize the information in a manner that serves them best, from a whole-hospital "heat map" to details of a singular collection. Additionally, alerts and updates may be delivered using a messaging system, and may include visual and auditory communications. These are only a few examples of its display capabilities.

Some embodiments may include a two-way communication capability between the user and the system 10. In this manner, a user can request specific information regarding collection, results, statistics, etc. They may also prompt the system 10 to perform additional assays or other functions if they perceive a need.

The display device 16 can be configured as any appropriate technology or combination of technologies. These may include smart phones, tablets, personal computers, wall-mounted monitors. These devices can be wireless or wired. As new display technologies become available, they can be integrated into the system 10.

Control System

Returning to FIG. 1A, the control system 18 is configured to manage the flow of information, in both directions, between the collection device 12, reader device 14, and display device 16. An example of the operation of the control system 18 is provided in detail below.

For example, the control system 18 is configured to receive pathogen sample information 20 from the reading device 14 where the pathogen sample information is related to a pathogen associated with a facility. For example, the pathogen sample information 20 provided by the reading device 14 can identify a pathogen sample type (i.e. a type of pathogen identified by the reader), a pathogen sample collection time, and a pathogen sample collection location of a given facility.

After receiving the pathogen information 20, the control system 18 is configured to correlate the pathogen sample information 20 with a pathogen transmission factor 22, such as stored in a database, the pathogen transmission factor 22 associated with transmission of the pathogen within the facility. In one arrangement, the pathogen transmission factor 22 can identify a variety of ways in which a pathogen can spread through a facility. The pathogen transmission factor 22 can identify patient demographics, hospital staff information, or cleaning protocols used, with respect to particular pathogens found in the facility.

For example, assume the pathogen information 20 identifies a particular pathogen as occurring in a given room of a facility, such as a hospital. In response to receiving the pathogen information 20, the control system 18 is configured to correlate the pathogen information 20 with a variety of pathogen transmission factors 22 (i.e., factors that affect how a pathogen is spread in the facility), such as a listing of the hospital nurses that have been in the room, identification of the movement of the patient relative to that room, and/or identification of the movement of hospital equipment relative to that room. In this case, assume the pathogen sample information 20 identifies the pathogen as C. Diff. and the location as Hospital Room 1. Also, further assume that the pathogen transmission factor 22 identifies a piece of medical equipment having been tested positive for C. Diff in the last two days. Based upon a correlation of the pathogen sample information 20 and the pathogen transmission factor 22, the control system 18 can identify the piece of medical equipment as possibly being the source of the spread of C. Diff.

Next, based upon the correlation of the pathogen sample information 20 and the pathogen transmission factor 22, the control system 18 is configured to transmit pathogen action information 24 associated with the primary pathogen sample information to an output device. While the pathogen action information 24 can be configured in a variety of ways, in one arrangement, the pathogen action information 24 is configured to inform a user about a condition regarding the pathogen sample information 20, thereby allowing the user to take some action regarding the pathogen. In one arrangement, the pathogen action information 24 can include information indicating a time to collect a sample, information indicating a location to collect a sample, information indicating a process by which to collect a sample, information indicating a type of sample to collect, and information indicating an instruction following collection, such as instructions related to the pathogen.

For example, as a result of the control system 18 receiving and correlating the pathogen sample information 20, the control system 18 can identify the presence of a pathogen in a given location in a facility, such as in a hospital room. In such a case, the control system 18 can provide, as pathogen action information 24, instructions to an end user to overcome issues raised by the presence of the pathogen. For example, the control system 18 can provide, as pathogen action information 24, instructions to remove the pathogen from the location by cleaning or by exposing the location to UV light to kill the pathogens. Alternately, the control system 18 can provide, as pathogen action information 24, instructions to select pathogen-carrying or pathogen-resistant patients or staff to access the pathogen-positive location. Accordingly, in the case where a pathogen is detected, the control system 18 is configured to provide, as the pathogen action information 24, instructions to an end user in order to remedy issues raised by the identification of the presence of a pathogen in a facility.

In another example, with reference to the scenario provided above, in the case where the control system 18 identifies a particular piece of medical equipment as possibly being the source of the spread of C. Diff, the control system 18 can provide a notice via the display device 16, as the pathogen action information 24, that the piece of equipment may be the source of the spread of the pathogen. Further, the control system 18 can provide, as the pathogen action information 24, a modified pathogen detection schedule, pathogen cleaning schedule, and/or an identification of the presence of the pathogen in the given room using a map of the facility provided by the display device 16. Each of these mechanisms provides information to a user about a condition of the pathogen sample information 20, thereby allowing the user to take some action regarding the pathogen.

As provided above, one arrangement, the control system 18 is configured to perform a number of functions. For example, the control system 18 is configured to provide pathogen action information 24, such as pathogen collecting instructions as described above, to an end user via an output device such as the display device 16. The collection methods, schedule of collections and other necessary information may be pre-determined and programmed into the controller 21. A schedule may be determined in a manner that assures that each room is audited, for example, every three days. If particular locations are more problematic than others, they can be scheduled for audit more often than others. As patterns are developed and recognized through the course of the ongoing audits, the control system 18 is configured to adapt and modify schedules to more effectively audit the facility. In some embodiments, this modification can be accomplished by the front-line staff responsible for remediation through an interactive display device, or may be the responsibility of an infection control officer or other staff member. In some embodiments, modifications are determined by algorithms within the control system.

As with the audit schedule, collection locations within a room can be pre-selected and then modified based on ongoing audit results. For example, initial locations may be based on recognized Critical Touch Points (CTP). CTPs represent areas of a facility touched frequently by multiple people, creating conditions conducive to the spread of HAIs. Some examples of CTPs include: bed frame, TV remote, bedside table, mirror, chair arm, door knob, trash can, IV pole, sink fixture, light switch, toilet fixtures, TP dispenser, Blood pressure cuff, shower head, and telephone.

The control system 18 is configured to modify all aspects of collection instruction over time, based on audit results, to improve efficiency of collection and value of results.

The control system 18 is also configured to correlate the results obtained by the reading device 14 (i.e., the pathogen sample information) with a pathogen transmission factor 22 associated with the transmission of a pathogen within a facility. For example, the control system 18 is configured to match each collected sample's result 20 with the location and time of collection stored in a database. If specific pathogen information is included in the test, that will also be correlated to the sample time and location.

The control system 18 is also configured to transmit and present the correlated information (i.e., pathogen action information 24) to the display device 16. For example, the control system 18 is configured to format the pathogen action information 24 into the desired visual representation as described above, and then send it in one or more formats to one or multiple display devices 16. In one embodiment, the control system's database resides in a cloud-based system rather than on a localized computer. In this manner, the control system 18 can manage information from multiple facilities, and data can be correlated between facilities.

Adaptive Learning

In one arrangement, the control system 18 is configured to continuously receive pathogen sample information 20 from one or more reading devices. In such an arrangement, the control system 18 is configured to utilize the information or data 20 to adjust a database of pathogen transmission factors 22 in order to adapt collection methods and locations based upon historical results (i.e. as associates with the pathogen transmission factors 22). This is an adaptive, self-learning system utilizing constant feedback to maximize the ability of the control system 18 to detect pathogens. The control system 18 can adapt collecting techniques to particular facilities or types of facilities, location within a facility, and type of room or even specific rooms and location within rooms. It can also take into account the pathogen types and their traits, such as locations that they are commonly found, etc.

For example, as indicated above and with respect to a first iteration of the process, the control system 18 is configured to receive primary pathogen sample information 20 from a reading device 14, correlate the information 20 with the pathogen transmission factor 22, and transmit pathogen action information 24 to an output device. In one arrangement, with reference to FIG. 1A, following transmission of the pathogen action information 24, the control system 18 is configured to receive secondary pathogen sample information 20' related to the pathogen associated with the facility.

For example, assume the case where the initial pathogen action information 24 instructs an end user to sanitize Hospital Room 1 because the presence of C. Diff. had previously been detected there. Following the cleaning process, the end user then collects a secondary pathogen sample from Hospital Room 1 using the collection device 12 and provides the sample to the reading device 14 for analysis. Following the analysis, the reading device 14 is configured to transmit the updated, secondary pathogen sample information 20' to the control system 18.

Based upon the secondary pathogen sample information 20' received from the reading device 14, the control system 18 is configured to update the pathogen transmission factor 22. For example, assume the case where the secondary pathogen sample information 20' identifies the continued presence of C. Diff. in Hospital Room 1. Based upon such an indication, the control system 18 is configured to update the pathogen transmission factor 22 (e.g., the pathogen transmission factor database) to indicate the continued presence of C. Diff in Hospital Room 1.

Next, the control system 18 correlates the secondary pathogen sample information 20' with the updated pathogen transmission factor 22, and based upon the correlation of the secondary pathogen sample information 20' and the updated pathogen transmission factor 22, transmits pathogen action information 24' associated with the secondary pathogen sample information to the output device, such as display device 16. For example, with the updated pathogen transmission factor 22 indicating a continued presence of C. Diff in Hospital Room 1 (i.e., following the sanitization of Hospital Room 1 as instructed in the first iteration) correlation of the secondary pathogen sample information 20' updated pathogen transmission factor 22 can cause the control system 18 to transmit pathogen action information 24' requiring the testing of other equipment in Hospital Room 1 to identify a source of the C. Diff contamination.

The control system 18 is further configured to continue the above described iterative process with subsequent secondary pathogen sample information 20' received from the reading device 14. Such a process allows the control system 18 to develop the pathogen transmission factors 22 (i.e., the pathogen transmission factor database) to maximize the ability of the control system 18 to detect pathogens.

In one example, as described above, audits may start with known CTP locations and a prescribed number of samples in a room. As results are compiled by the control system 18, the number of samples and their locations can be fine-tuned so as to sample the locations most likely to return a positive result. If, for example, a particular location generally returns a negative result, the control system 18 may limit or stop future collection at that location, and instead collect at an alternative location, or eliminate that collection entirely. If a particular location generally returns a positive result, the control system 18 can add or relocate samples in future collections to locations that have similarities. For example, if a pathogen is found on a piece of equipment in a room, the control system 18 may test other equipment in the room. The control system 18 may also decide to test similar equipment in other rooms. It can be seen that this system 18 will help to fine tune its detection capabilities to develop testing protocols that will sample the locations most likely to return a positive result. If the particular pathogen found is included in the data, the testing can be tuned to test for the most troublesome pathogens.

In one arrangement, when the control system 18 is initially brought online, the system 18 is configured to compare and contrast the results of sample type, location and result (i.e., pathogen sample information 20) with the pathogen transmission factor 22. As the database of pathogen transmission factor results 22 grows, the control system 18 is configured to analyze the database to recognize patterns and trends in the data 22 and to analyze patterns within patterns. As additional information is entered into the control system 18, such as patient demographics, hospital staff information, cleaning protocols used, etc., these variables can be analyzed within the context of results for an in-depth understanding of complex interactions. As the database grows and algorithms evolve, the control system 18 can become predictive. With the ability to predict future trends, the system will tailor auditing methods to find contamination at the earliest possible stage.

In some embodiments, control systems may be interlinked. This can include multiple control systems 18 sharing a database, or a centralized control system 18 supporting multiple facilities. One advantage of interlinking is that as each control system 18 evolves, it can share its learning with the others, improving the performance of auditing at all facilities. Another advantage of interlinking is the ability to compare patterns and outcomes between facilities. For example, a series of events at one facility may have preceded an outbreak. The pattern is recognizable and becomes part of the system's database. The control system 18 can look for the beginnings of this pattern in other facilities and take steps to avoid an outbreak there. Interlinking can take place within floors of a facility, between local facilities, regional facilities, or even national or worldwide facilities. These are only examples of the benefits of interlinking.

In some embodiments, the control system 18 is configured to collect information about the cleaning methods and protocols that are used in response to a positive pathogen result. This data can be used to correlate the audit results with the efficacy of the cleaning methods. The employee performing the cleaning may, for example, enter cleaning information into the control system 18. This information may include cleaning chemicals used, method of cleaning, specific items and location cleaned, etc. This information may be entered using any of the communication devices previously discussed. The control system 18 can compare cleaning methods to audit results and build a database of the most effective responses to pathogen contamination. As the control system 18 learns (i.e., builds the database with most effective responses), it may display suggested cleaning methods along with the pathogen location information.

In one arrangement, the control system 18 may perform comparative analyses. For example, results obtained both from collecting samples (i.e., pathogen sample information 20) and from analyzing cleaning methods can be compared between the technicians who performed the collection and/or cleaning. If, for example, a technician's results are notably different from the norm, it offers an opportunity to improve the results by learning effective methods from higher performing technicians, and by increasing training for lower performing ones. These comparisons may also be made between locations such as floors, departments, facilities, regions, etc., and by shift, day, season or any other distinction that can help the system learn and understand the cause and effect of behavior vs. performance.

If the control system's database contains data 24 from multiple facilities, that data can be compared and trends can be analyzed. Recognizable patterns may develop, providing an understanding of the trends of pathogens and their spread. These patterns can be used to predict the location and type of pathogen and help to guide audits. The control system 18 may also obtain the ability to predict future outbreaks by recognizing a set of conditions that are conducive to an outbreak, and therefore facilitate its prevention. This is particularly valuable and effective when the control system 18 is connected between facilities as it may see potential problems that can affect facilities around a region.

In some embodiments, the control system 18 may have access to certain of the facility's own data. This can be through a direct link to the facility's electronic medical records, or by way of limited anonymous data compiled specifically for use by the system. Data that is obtained may be used to determine trends by interlinking it with information acquired during auditing. These trends are used to improve audit effectiveness and to ultimately make predictions and conclusions that will aid in the prevention of HAIs and disease outbreaks. Trends can be followed and linked geographically by room, department, facility, region, etc., demographically by patient status, diagnosis, history, etc., and chronologically by time, date or season.

In some embodiments, it can be advantageous to the control system 18 to understand the human and/or equipment traffic entering and exiting a patient room or other location. This may be as simple as counting the total number of visitors to a monitored location using a commercially available proximity detector, camera or other device capable of recognizing that a person or piece of equipment has passed through a doorway. In this manner, the control system 18 is configured to correlate the presence of pathogens to the total quantity of staff and other visitors entering the space. This correlation may show that high traffic areas have a higher probability of pathogen contamination than low traffic areas. This information can be used to adapt collection quantities, locations and techniques. The control system 18 can utilize total traffic counts within a time period, or look at traffic vs. time of day to obtain and understand trends.

A traffic-identifying system may include recognition of the traffic entering and exiting the space. For example, staff member's badges may include an RFID tag or other device that allows the system to specifically identify them as they enter or exit the space. In this manner, the system can determine any correlation between particular staff members and pathogen presence. Visitors may be issued badges with similar capabilities.

The control system 18 may utilize a camera-based system. Such a system may include facial recognition or other techniques to identify staff, patients, visitors, etc. Additionally, people's motion may be detected and analyzed. There are systems currently available that have the ability to do this. Examples of this technology include Echo5D™ by Atlas5D™, as well as the Kinect Sensor. By including this capability, the system can determine motion within the space, and may monitor contact between the patient and medical staff and visitors, medical equipment and other surfaces within the patient's environment. All of this information may be used by the system to understand interrelations between all these variables and employ the findings for the prediction of pathogen locations.

Any information obtained by the control system 18 may be used to generate more effective auditing. This can be include adding the diagnosis of the previous patent. In this manner, audit results can be compared to patient diagnosis data. For example, after a patient discharge, if the prior patient had MRSA, it could trigger a different audit protocol than if the patient had a different, or no infection. As more data is acquired by the control system 18, the results will continue to improve. This data can be patient related, such as demographic statistics, or may be related to the facility's staff, such as the doctor, nurses, cleaning staff and other employees. This can show trends pertaining to specific workers. The same is true for the geographic locations within a facility showing, for example, that a particular room, floor, department, etc., has more or less propensity for pathogens. Chronology can add an additional dimension of detail, as trends can be followed by time of day, season, etc.

With these factors considered, the number of samples and their locations for any room audit can change in real time based on the history of that particular room, its patients, staff and any other contributing data. The control system 18 may even be configured to take into account health related information from other locations within a facility, or within other facilities in the immediate geographical area, within the region, or even a wider area.

In one arrangement, mathematical prediction methods can be developed and improved with practice of embodiments of the current innovation. As an example, the control system 18 configured to execute a discriminant analysis may be used to predict the probability of pathogen presence. This probability can then be used to determine collection location, type frequency, etc. An example equation can be shown as: Probability of pathogen presence=$P(PP)=\alpha+\beta_1X_1+\beta_2X_2+\beta_3X_3+\beta_4X_4\ldots$, where $X_1$, $X_2$, etc. are the variables as described above and can include collection results such as pathogen presence, type quantity, etc., patient demographic, staffing, cleaning protocols used, traffic and others. $\beta$ values are weighting values for each of the variables. The weighting values will be determined and modified over time as results are correlated and understood. This is merely an example of the type of equation that may be used by the adaptive, predictive control system 18. Depending upon pathogen detection results, formulas may change over time, as may weighting values and included variables.

In some embodiments of this innovation, the control system 18 can be configured with the ability to direct cleaning and remediation efforts that are determined by audit results. With knowledge of the particular pathogens that were detected and their location, specific and targeted cleaning methods can be determined. This can employ the most efficacious cleaning chemicals and methods to use for a given pathogen on a given surface. For example, if C. diff is found on a bed rail, the system may know that the best way to remediate it is with a bleach wipe. Depending on the pathogen to be removed and the surface on which it is found, the best methods and cleaning chemicals can be determined. This cleaning information may be communicated to the staff via the display.

In some embodiments, this control system 18 can be configured to specify the use of targeted cleaning kits. Kits can be designed that contain chemicals, cleaning tools and instructions necessary for cleaning a specific pathogen on a specific surface. In the previous example of C.diff found on a bed rail, an individually identifiable kit could contain bleach wipes and instructions for cleaning. Other individually identifiable kits can contain chemicals and cleaning supplies for any number of pathogens and surfaces. The use of kits in this manner can help to ensure thorough disinfection and simplify the cleaning process. Additionally, the system may determine that an alternative sanitizing method such as room fogging or other whole-room sanitizing method would be most effective.

Additional steps may be taken to assure the quality and effectiveness of audit results. These can be used as a method to certify collection technicians, audit results and facilities. These steps are a series of checks and balances that add confidence to the validity of the audit.

Collection technicians can be trained and certified in the proper use of devices, testing methods and protocols, as well as ethical and performance standards. Only certified staff with proper identification may collect samples. These staff members may be hospital employees; however, it may be preferable for them to be employees of an independent auditing company. This provides impartiality and can add confidence to the audit results.

The control system 18 can compare audit results from the certified staff members. If a collection device 12 has notably different results from a statistical norm, it may be an indication of a performance problem that needs to be addressed. The control system 18 can look at percentage of negative results, amount of time taken for collections, etc. This step provides an additional level of confidence in the audit results.

An independent laboratory may be used to verify the results of the system's reader device 14. A percentage of samples that have been read may be sent to the laboratory to be analyzed. The percentage of samples can be a fixed amount, say 10%, can be variable based on results, or can be determined by an appropriate statistical sampling method. The laboratory's results are compared to the reader device's results as one more check on the system.

A collection device 12 may be used that contains a control sample. For example, the collection device 12 may contain two compartments, one for the collected sample and one containing the pathogen being studied. This is can be configured as a simulated, inert version of the pathogen. The control sample should always return a positive result. If the result of the control is negative, it indicates that the reader is not performing correctly. A positive control sample result adds to the confidence of collected sample's result.

Pathogen Detection

Taken together, the collect and read functions of the collection device 12 and the reader device 14 can form a pathogen detection system. Conventional detection methods run the gamut from simple products that determine if a spot has been cleaned to sophisticated scientific methods such as spectroscopy and DNA testing. By contrast, embodiments of the control system can use any applicable technology to detect the presence of harmful pathogens, breaches in cleaning protocols or other indicators of potentially harmful conditions. Embodiments of the innovation are not dependent upon a specific technology. As improved detection methods and devices are developed, they may be incorporated into this system.

Pathogen detection methods that can be utilized by the current innovation vary widely in the length of time needed to obtain results, from minutes to days. Although faster methods can be advantageous, even the slowest methods have value. Immediate results are not as critical to the system's efficacy as is the value of an ongoing audit. The continuing stream of pathogen data will provide an understanding of the level of accumulation of pathogens in terms of presence, persistence and quantity. This is particularly true in the prevention of outbreaks, since it takes a number of days for an outbreak to occur, and even the slowest methods allow for detection and remediation substantially before that time. With an average hospital stay of 3.6 days, results can be obtained before an infection is spread from one patient to the next. This alone can substantially decrease the occurrence of HAIs.

Even in its simplest embodiment, the current innovation can have a tremendous effect on the incidence of HAIs, saving many lives and billions of dollars. In a health care facility, where infections are commonplace, it is often ordinary practice that the occurrence of three patient infections triggers an action for infection control and remediation. This means that a hospital room that is contaminated with a pathogen can cause three HAIs before it is attended to. An example scenario for the current innovation will use the following assumptions:

⅓ of hospital rooms will be audited each day, meaning each room is audited every 3rd day.

The pathogen detection test returns results in a maximum of 3 days. This is the slowest of the current technologies.

Audit results for each room are received every 3 days, reporting pathogen contamination from 3 days prior.

The average patient stay is 3.6 days.

The result is that even with a 3 day return of test results, on average only 1 patient can be exposed to pathogen contamination. That is one patient exposure compared to the current 3 patient infections. This means that the current innovation, in its simplest form, can reduce the occurrence of HAIs in an audited room by ⅔.

To further illustrate, an example timeline will be presented:

Day 1. Audit sample (1) is collected. Later in the day, a patient is admitted. This patient (1) is an asymptomatic pathogen carrier who subsequently contaminates the room.

Day 4. Audit sample (1) returns a negative result. Audit sample (2) is collected. Patient (1) is discharged. Another patient (2) is admitted.

Day 7. Audit sample (2) returns positive for pathogens. Patient (2) has been exposed, but may not yet be symptomatic (It can take from 2 days to over a week for incubation). If patient is deemed susceptible, antibiotics may be started. The room is remediated.

This nearly worst-case scenario illustrates that the current innovation, even in its simplest form and using the slowest test methods, can be extremely effective. Even though patient (2) was exposed, the exposure was detected prior to the patient's discharge. Treatment can begin, and the patient can be discharged on schedule. Without the knowledge gained from the audit, this patient could have been discharged and become symptomatic after returning home, resulting in a costly readmission. The delay in treatment may have resulted in a severe infection, causing a lengthy stay in the hospital, or even death. Additionally, without the continuing audit, two additional patients may have been infected prior to remediation.

Table 1 shows the above scenario along with modifications and illustrates the effect of collecting samples more frequently and using tests that can return a result in one day. The results in bold indicate positive results. All results are based on an average length of stay. As would be expected, the best results occur when the room is sampled every day using a test with a one day result time. In this case, pathogen contamination is discovered prior to patient 1 being discharged. The other scenario that, on average, may return a positive result prior to patient 2 being admitted is to sample every two days with a one day test result (depending on the time of day that the result is received). All the other results are received between one and four days after patient 2 is admitted.

TABLE 1

| | sample frequency (days) | | | | | | |
|---|---|---|---|---|---|---|---|
| | 3 | 3 | 2 | 2 | 1 | 1 | |
| | result time (days) | | | | | | |
| Day | 3 | 1 | 3 | 1 | 3 | 1 | |
| 1 | sample 1 | sample 1 | sample 1 | sample 1 | sample 1 | sample 1 | patient 1 admitted |
| 2 | | result 1 | | result 1 | sample 2 | sample 2 result 1 | |
| 3 | | | sample 2 | sample 2 | | result 2 | |
| 4 | sample 2 result 1 | sample 2 | result 1 | result 2 | result 1 | | patient 1 discharged patient 2 admitted |
| 5 | | result 2 | sample 3 | | result 2 | | |
| 6 | | | result 2 | | | | |
| 7 | sample 3 result 2 | | | | | | |

The above scenario does not take into account additional factors. Current research shows that the probability of a patient becoming infected by contamination in a room appears to be related to the percentage of surfaces within that room that are contaminated. Additionally, the quantity of bacteria present on a contaminated surface contributes to the probability of the pathogen being spread. The more massive a bacteria colony is, the more likely it is to be contacted and to cause infection. The opportunity for the spread of contaminants increases with time as the patient, visitors and staff touch multiple surfaces, depositing and/or spreading pathogens, and pathogen colonies have time to grow. The length of time it takes for the contamination level to reach a point of high probability of transmission is variable and uncertain, but it may take days to weeks for the level to become critical. This makes the current innovation even more effective because pathogens may be found by an audit before having enough time to spread and grow, creating a high probability of infecting a patient. Even with a 3 day audit result, many pathogens will be found and remediated when their levels are low and not likely to cause infection.

The choice of sample frequency, and the resulting cost increases will be determined by factors such as staffing levels, costs of testing and, mostly, effectiveness as determined by the evidence produced by the scientific audit. The choice of sampling frequency and protocols for a particular facility or location within a facility may involve additional factors. Some areas, such as day surgery, emergency rooms, urgent care facilities, etc. will have a shorter length of stay than the 3.6 day average, as well as exposure to more patients. It may be advantageous to sample more frequently and/or choose more rapid detection methods in these areas. In contrast, a chronic or other long term care facility may not need to be audited as often. Facilities that work largely with patients that have compromised immune systems, such as oncology, can require more frequent audits than a physical therapy department that works with injured, but generally healthy patients. These are illustrative examples, and not an exhaustive list. Any factors that contribute to the spread of pathogens and resulting infections may be taken into account.

With most technologies currently available, a detection method can generally test for only one type of pathogen. The particular pathogen being audited must be determined prior to testing. For example, C.diff, which may account for as much as 30% of HAIs, may be of particular interest within a facility. Even if this were the only pathogen being tested for, the system would still be effective. Where C.diff is found, there are likely to be other pathogens. Additionally, C.diff is a difficult pathogen to remove. If an area has been cleaned well enough to remove C.diff, then most other pathogens have also been removed. Because of this, the result of testing for C.diff alone can be substantially greater than 30%.

Testing for specific pathogens may be location dependent. If a facility, or location within a facility, historically shows a more significant occurrence of a different type of infection, for example MRSA, then it may be more effective to sample for that pathogen. The selection of pathogens to test may also change with time, as different ones become predominant. Audits may be chosen based on historical information, for example, if a room's prior patient had an infection that may cause an HAI, the next audit for that room may test for that specific pathogen. Numerous testing methods can be developed as the auditing system is used. For example, target pathogens may be alternated during subsequent audits, or more than one target pathogen may be sampled in an audit. As testing technologies become available that can sample for multiple pathogens, they can be incorporated into the current system.

Patient Perimeter

Figure 10A:
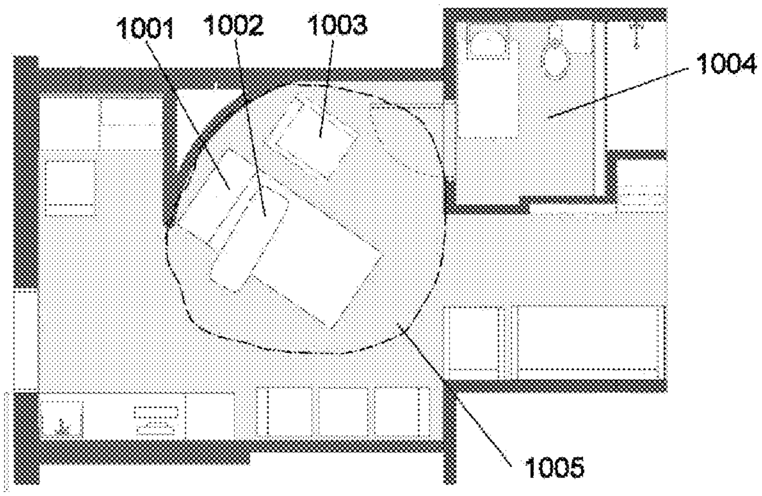
FIG. 10A illustrates a patient perimeter for a bedridden patient.
Figure 10B:
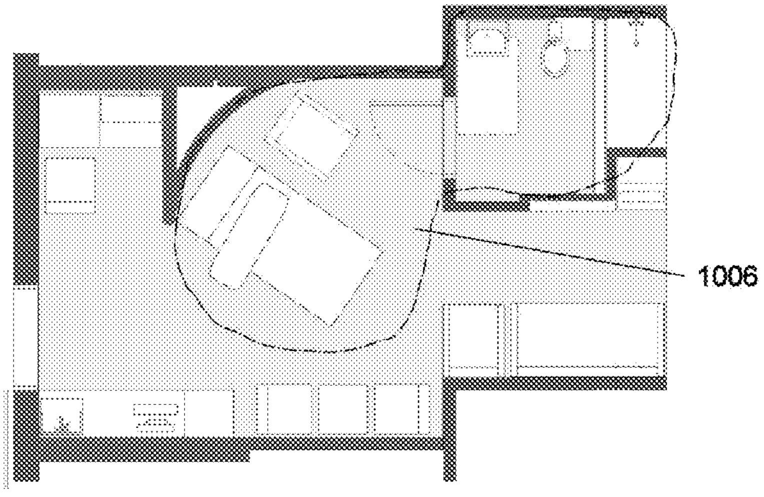
FIG. 10B illustrates a patient perimeter for a patient with limited mobility.

A patient may contact environmental pathogens by touching surfaces, people or other items that are contaminated. Accordingly, important locations to sample are those within the patient's reach. A patient's condition may be taken into account by the system in order to refine sampling by defining a patient perimeter. A patient who is confined to a bed can only reach a limited distance, and so has a small perimeter in which to make contact with pathogens. In one arrangement, the system can confine sampling to locations within reach of the patient, such as the bed, table, IV pole, night stand, telephone, TV remote, etc. A patient with limited mobility may get out of bed only to use the bathroom. Knowing this, the control system 18 may expand the perimeter to include any surfaces or objects between the bed and bathroom, as well as inside the bathroom itself. In the case of an ambulatory patient, the perimeter may expand to include the entire room. In a unit with ambulatory patients, the patient perimeter may expand to encompass hallway surfaces, equipment, etc. FIGS. 10A and 10B depict a hospital room. Within it are the bed 1001, table 1002, stand 1003 and bathroom 1004. For the bedridden patient, the patient perimeter may be defined as shown 1005 in FIG. 10A. For the patient with limited mobility, it may be defined as shown 1006 in FIG. 10B. For the ambulatory patient, the entire room may be defined as the perimeter.

In one arrangement, the control system 18 is configured to define a patient perimeter 25 as a pathogen transmission factor 22 associated with a patient location within a facility, such as based upon the above-referenced criteria. Defining the patient perimeter allows the system 10 the ability to perform the most effective and cost-efficient sampling possible. For example, the control system is configured to transmit pathogen action information 24 to an output device based upon the correlation of the pathogen sample information 20, the pathogen transmission factor 22, and the patient perimeter 25. By defining the perimeter, the pathogen action information 24 can indicate that areas that are not likely to infect a patient are not sampled, saving time and cost. In a smaller perimeter with less area and surfaces, it may be an advantage to sample a higher percentage of surfaces to increase the confidence of the results, since a sample area with a small perimeter may take less time and fewer collection samples. In many cases, a small perimeter may indicate a compromised patient with a weak immune system. More concentrated sampling can give a higher confidence of a pathogen-free environment. As a patient's status changes, the system may adjust the patient perimeter to suit. For example, a patient perimeter can be classified based on mobility and/or on diagnosis. The patient perimeter can also change with time.

In a room that contains more than one patient, the control system 18 may consider the status of all patients when determining appropriate sampling methods and locations.

Figure 11:
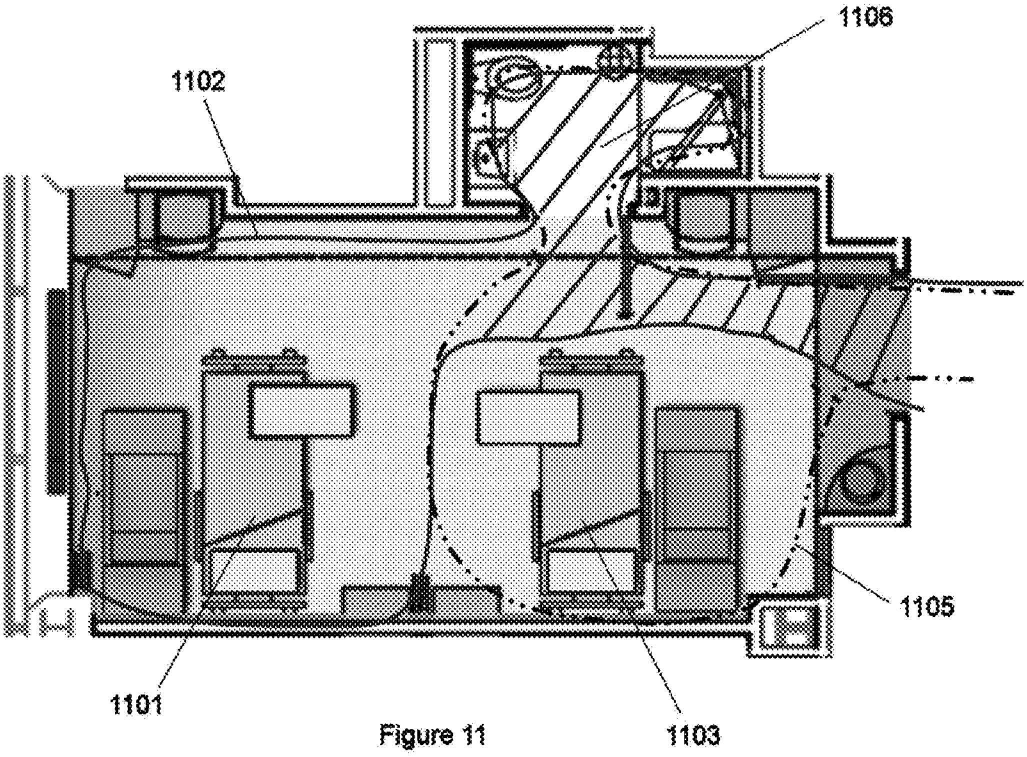
FIG. 11 illustrates an example of a double room in which both patients are ambulatory

FIG. 11 shows one example of a double room in which both patients are ambulatory. The patient in the first bed 1101 has a patient perimeter depicted by the solid line 1102. The patient in the second bed 1103 has a perimeter depicted by the broken line 1105. The area where the two patient's perimeters overlap is shown by hatch lines 1106. The overlapping area includes the bathroom and the aisle in front of the second bed. The control system 18 may determine that the overlapping area requires more stringent auditing then the non-shared areas. This may include sampling more area of the surfaces, sampling additional surfaces, testing for multiple pathogens, more frequent auditing, etc. Other factors may be included in sampling decisions. For example, since all persons entering or exiting the room must pass through part of the perimeter of the patient in the second bed, additional or alternative testing may be conducted in that patient's area. The health of the individual patients or even the previous patient's diagnosis may be incorporated by the system for use in determining sampling techniques. These are only examples of the use of a patient perimeter as an element in determining sampling techniques and frequencies. These methods may be used with rooms with more than two patients, with alternative room layouts and floor plans, or in combination with any other methods described in this disclosure.

Other perimeters may also be defined, such as hallways and common areas, diagnostic rooms, etc. These perimeters will be defined as zones. The zones in this example are not a complete list, but are useful to illustrate aspects of this innovation. Zones may be added, subtracted of changed as needed, depending on an individual facility, type of treatment, etc. For this example, zones will be defined as:

Zone 1: perimeter of a bedridden patient (1005 in FIG. 10A)

Zone 2: perimeter of a patient with limited mobility (1006 in FIG. 10B)

Zone 3: perimeter of an ambulatory patient; the entire room, including bathroom

Zone 4: areas shared by more than one patient (1106 in FIG. 11)

Zone 5: unit hallways and common areas

Zone 6: diagnostic or treatment areas (X-Ray, PT, etc.)

These zones may be used in a patient centered approach to determine when and where to collect samples to most efficiently and effectively find and aid in the removal of pathogens. A patient can be classified as a Zone 1, 2, or 3 patient as described above.

An auditing protocol may be defined for each zone. For example, a Zone 1 auditing protocol (AP1) will order samples to be collected on the critical touch points within reach of a Zone 1 patient. In embodiments utilizing an adaptive system as described previously, the sampling points may change with time, based on the results of previous collections. A Zone 3 auditing protocol (AP3) will include sample locations within the entire room and bathroom. This is similar for all zones. Some embodiments may include multiple protocols for each zone. There may be a standard protocol along with an enhanced protocol that includes more detailed sampling or pathogen-specific sampling based on a patient's susceptibility, sample result history or other factors. For example, a standard Zone 1 audit protocol may include sampling a total area of 20 square inches on the bedrails, table and IV pole. If a Zone 1 audit tests positive, the system may trigger an enhanced audit protocol that samples 50 square inches of surface on the standard audit surfaces plus others. If a patient being admitted is deemed to have a high susceptibility of infection, or if the prior patient had an infection, it may also trigger an enhanced or expanded audit. There can be multiple audit protocols for each Zone that are targeted to specific pathogens, patient susceptibilities, prior history and other factors.

In some embodiments, the system can initiate a remediation protocol based on audit results. Cleaning and sanitizing protocols can be developed for each zone. For example, a Zone 1 remediation protocol (RP1) will encompass the cleaning methods, tools and cleaners necessary for an intensive sanitizing within that zone. This is similar for all zones. There may be more than one protocol for each zone. The choice of protocol may be based on the specific pathogen found or other parameters. Additionally, enhanced protocols with more rigorous remediation techniques may be used in Zones that have a persistent or large volume contamination.

In some embodiments, the materials and supplies for each auditing and/or remediation protocol may be prepared in kit form. For example, the system may instruct the user to acquire an AP1 kit and proceed to a specific room to collect samples. The AP1 kit may include collection devices 12 and instructions necessary to take samples in Zone 1 of that room. Similarly, the system may send an instruction to acquire a RP1 kit, containing the necessary chemicals, supplies and instructions, and proceed to a specific location to perform a remediation.

Figure 17:
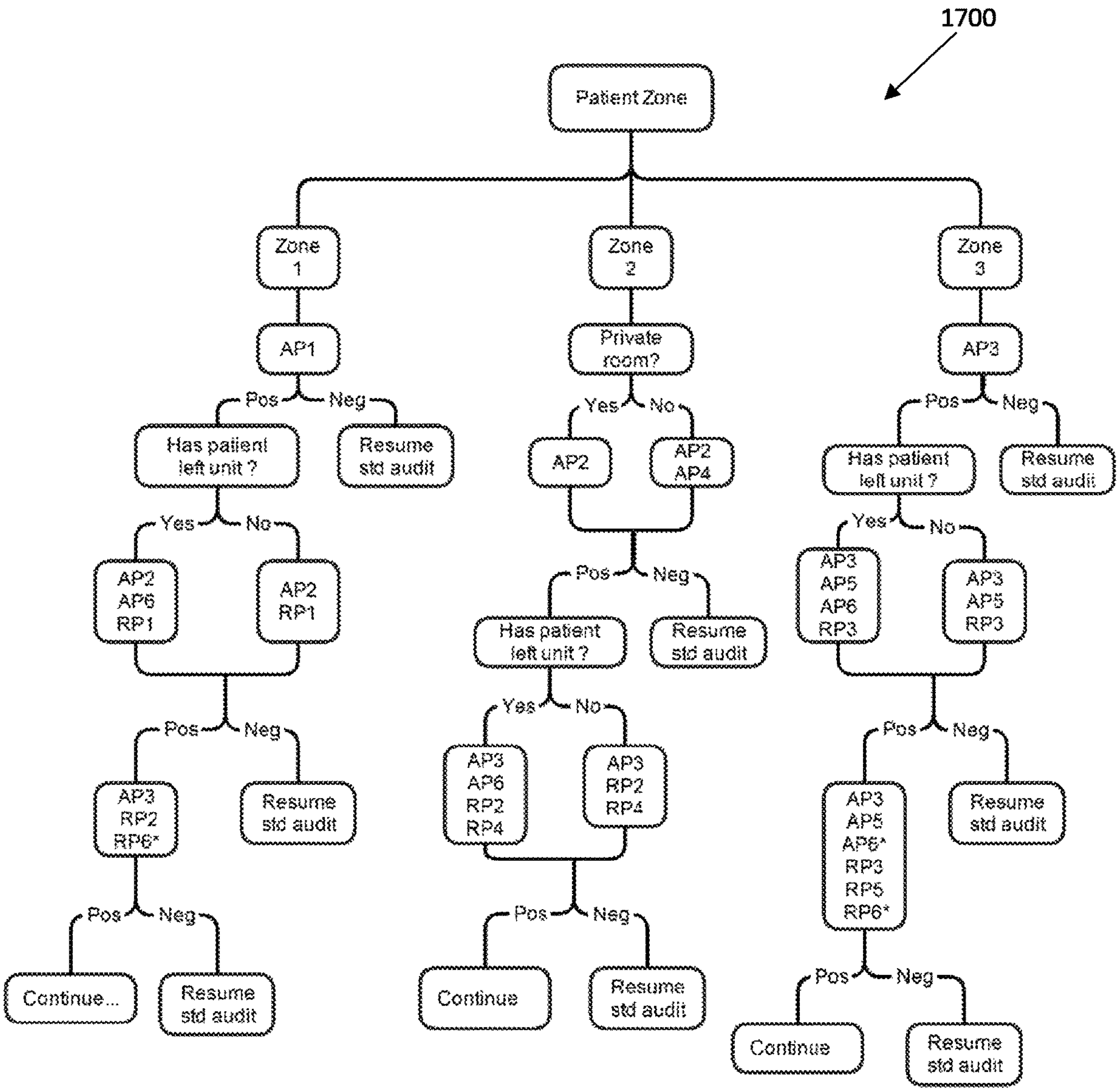
FIG. 17 is a flowchart that illustrates a decision path for each zone.

The flow chart 1700 in FIG. 17 shows a decision path for each of the zones. This example shows both auditing and remediation responses, however some embodiments may include auditing only. For simplicity, only one auditing protocol and one remediation protocol is shown for each zone. These are simplified examples. It may be preferable to include additional factors in the decision tree. These may include patient diagnosis, pathogen results and history, multiple protocols for each zone, etc.

Referring now to FIG. 17, each patient's zone is defined as Zone 1, 2 or 3 as described above. For a Zone 1, or bedridden patient, AP1 is deployed. A negative result indicates there is no pathogen contamination. In this case, the standard auditing schedule is continued. A positive result indicates the presence of pathogens, which can require further action. It may be important to know if the patient has left the unit, for example has been transported for X-Rays, physical therapy, etc. If the patient has been to another location, it may be necessary to test that location to determine whether pathogens have been carried there by the patient. If so, the system can order the deployment of AP2 (expanding to the next zone) and AP6 (the visited location). If the patient has not left, then only AP2 is necessary. At this point, RP1 may be deployed to remediate any pathogens in Zone 1 of the patient room. If the sample results are negative, the standard audit is resumed. If the results are positive, the audit area is expanded to Zone 3, remediation expands to RP2, and if positive at the remote location, RP6. Negative results always return the system to the standard auditing protocols. Positive results can trigger expanding sample and remediation zones.

For a Zone 2 patient, with limited mobility, the control system 18 may inquire whether the patient is in a shared room. If so, then Zone 4 (the shared space) can be included in the auditing and, if necessary, remediation protocols. For a Zone 3 ambulatory patient, the standard audit zone is expanded to the entire room SP3. Since this patient has access to more spaces, a positive result may require auditing and remediating the unit hallways and common areas.

These examples show only one timeline that may span multiple days. The standard auditing procedures may test each room daily, every 2 days, etc. For each patient or room, there may be multiple timelines at various points in their progression. The results from one timeline may be used as a factor in making auditing and remediation decisions in concurrently occurring timelines.

Detection Technologies

Following is a synopsis of several conventional pathogen detection technologies. The current innovation may incorporate one or more of these, or other, pathogen detection technologies.

ATP tests can reveal biomass left on a surface, and results are available in minutes. A disadvantage with ATP testing is that it indiscriminately detects biomass and cannot tell the difference between living or dead cells, or whether a detected biomass is harmful or benign. This can result in a great deal of cleaning effort to remove harmless substances. Another technology would recognize and possibly identify and classify pathogens.

One conventional method used in healthcare facilities is to culture samples taken within a room that is suspected of being contaminated. An area is swabbed for a sample, which is then placed into a growth medium such as agar. The sample is incubated at an elevated temperature and observed for bacteria growth. Various growth media and techniques may be used to test for a variety of pathogens. As the pathogen colonies grow, the morphology of the growing colony is observed and the type of microbe is determined. Initial results can begin to be seen in approximately six hours, but it can take up to 48 hours to make a positive identification. This method relies on the experience of the observer to make a correct identification. It can, however, obtain detailed information about the type of pathogen found.

Gram staining is a conventional method of classifying bacteria. This is a manual process in which a sample is prepared and then viewed under a microscope. The multi-part preparation includes smearing the sample onto a slide, covering with crystal violet, rinsing, covering with Gram's iodine (mordant), draining then rinsing the slide in 95% ethyl alcohol, rinsing, covering with safranin (counterstain), rinsing and blotting. The prepared sample is viewed under the microscope, and bacteria are identified by color and shape, and are classified by gram positive or gram negative. Gram positive bacteria stain violet and include *Bacillus, Listeria, Staphylococcus, Streptococcus, Enterococcus*, and *Clostridium*. Gram negative bacteria stain red, and can include *E. coli, acinetobacter, Klebsiella pneumonia* and others that result in many types of HAIs, including pneumonia, urinary tract infections, and bloodstream infections.

Liquid chromatography-mass spectrometry can be used to identify microorganisms. A sample is first separated by liquid chromatography, where a pressurized liquid and a sample mixture are pumped through a column filled with a sorbent, which separates the sample components. The components are then analyzed by the spectrometer, which breaks down the light emitted or absorbed by chemical elements into specific lines of color. Every chemical element on the periodic table has its own spectral fingerprint that identifies it, so the chemical compounds can be identified. In two of the more commonly used methods, Raman spectroscopy measures the scattering of light, while infrared spectroscopy is based on absorption of photons. This technique is rapid and accurate, but the equipment is very expensive, costing $80K and up per unit.

DNA testing can be used to identify microbes. One method of DNA testing utilizes a CCD camera for Surface Plasmon Resonance imaging (SPRi). This is an optical process used to detect the binding of molecules onto arrays of probe biomolecules attached to chemically-modified gold surfaces. In basic terms, the camera looks at light refracted through a prism and a computer creates a DNA image from the information.

In one arrangement, optics-based instant read scanning devices can also be utilized. For example, optics based devices can illuminate a microbe with specific wavelengths of light and detect optical phenomena specific to pathogens.

Collection Device

Figure 12:
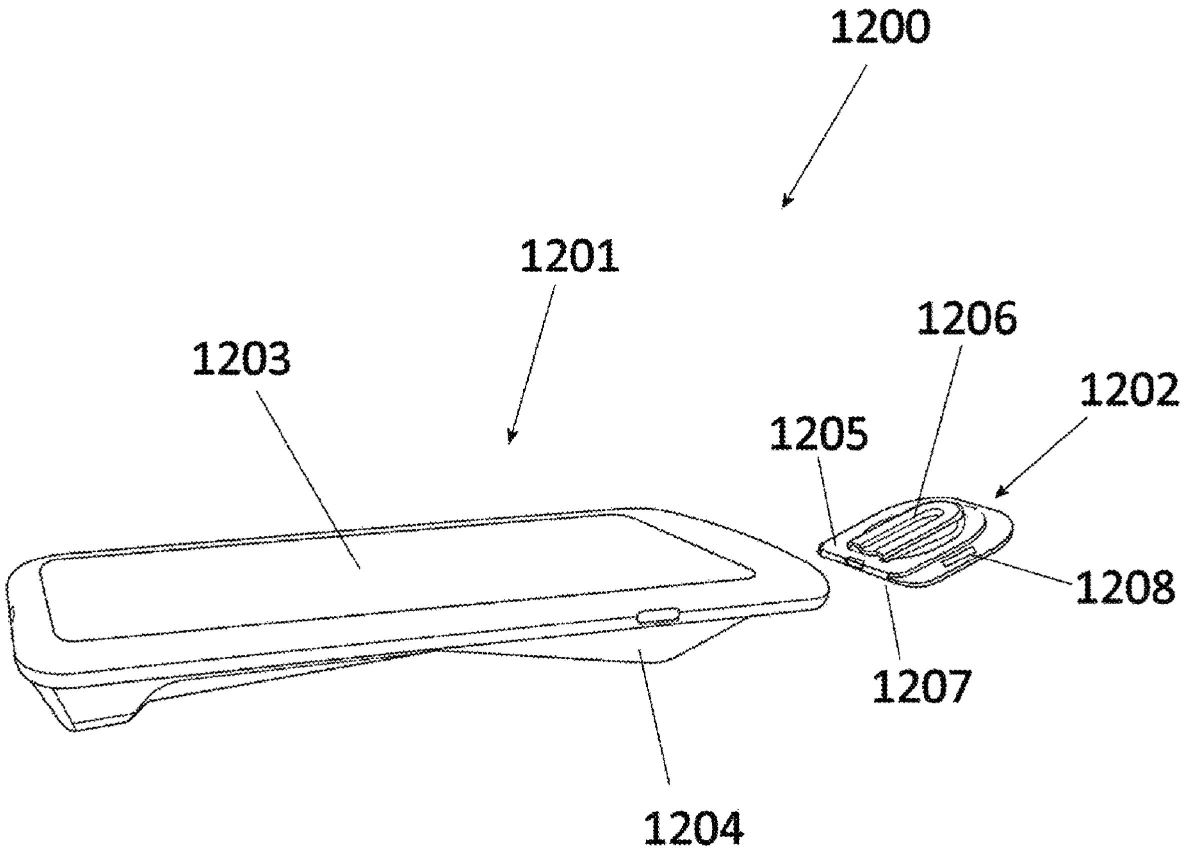
FIG. 12 illustrates a collection system having a collecting device and a replaceable collector, in one arrangement.

Accuracy and consistency of sample collection is critical to obtaining legitimate pathogen testing results. Some embodiments of this innovation may utilize a sample collection device 12 that will assist the user in collecting samples at the correct locations, at the correct time, and with proper collecting techniques FIG. 12 shows an example collection system 1200 having a collection device 1201 and a replaceable collector 1202. In one arrangement, the collection device 1201 includes a user computerized device, such as a smartphone 1203 and a smartphone housing 1204. A commercially available smartphone, such as an iPhone, Android, etc., may be used, since these devices contain many of the features that will aid in collecting samples. However, a custom designed device could also be used. The smartphone 1203 may be inserted into the housing 1204 in the same manner as it is inserted into a protective case. The housing 1204 allows the user device 1203 to interface with the replaceable collector 1202 and may contain additional electronic and/or mechanical components and connections.

The replaceable collector 1202 contains a swab component (not visible in this view) that is wiped on the surface being sampled. The collector 1202 comprises a body 1205 with an attaching means 1206 to removably attach it to the housing. In this example, the collector body 1205 has a hinge 1207 that allows the body to open, exposing the swab. In one embodiment, the collector 1202 is automatically identifiable by the collecting device 1200. This example utilizes a bar code 1208 that can be read by the smartphone. Other identifiers may be used, such as QR codes, RFD or other suitable technology. The shape, attaching mechanism and other details of the collector 1202 are exemplary and not meant to be limiting. Other designs can function as well within the scope of this innovation.

Figure 13A:
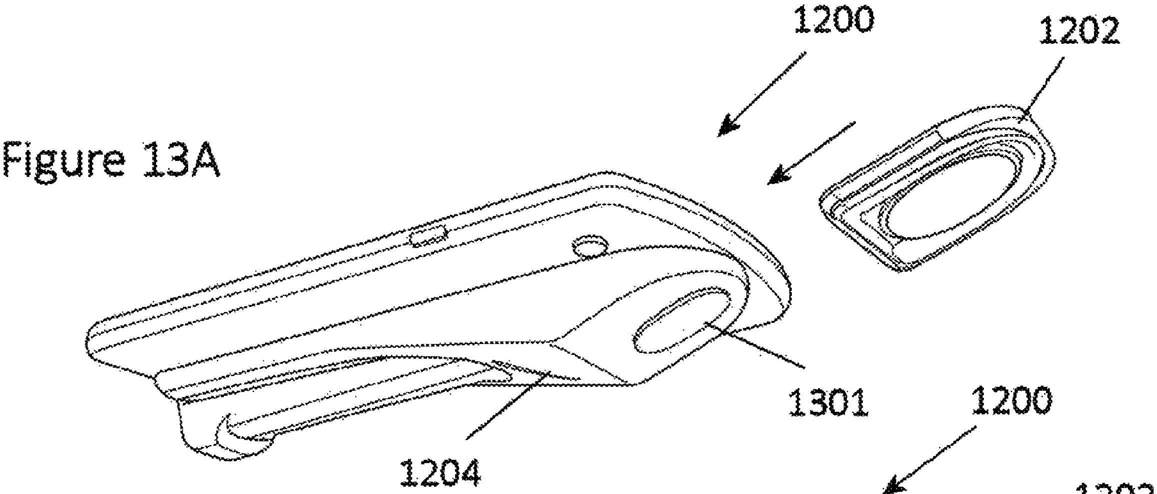
FIG. 13A illustrates an exploded view of the collection system of FIG. 12.
Figure 13B:
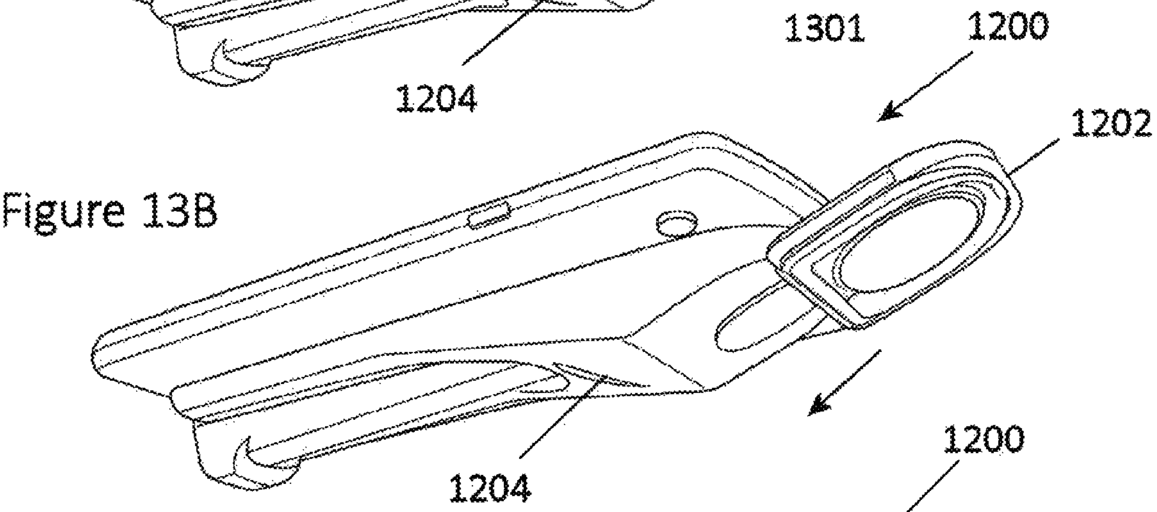
FIG. 13B illustrates attachment of a collector to a housing of the collection device.
Figure 13C:
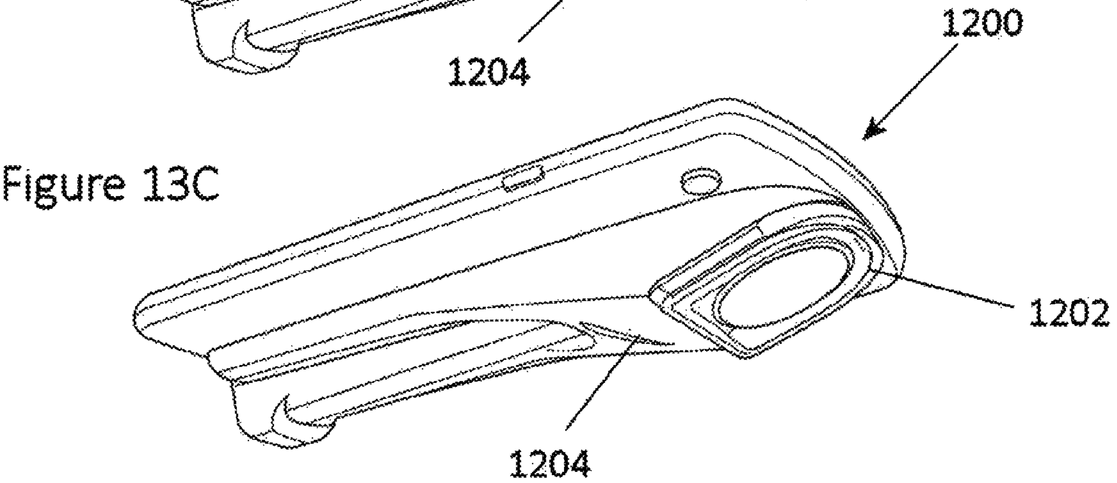
FIG. 13C illustrates the collector attached to the collection device.

FIGS. 13A through 13C illustrate the progression of the attachment of the collector 1202 to the computerized device housing 1204. In this case, a tab 1301 mates with the slot 1206 in the collector 1202. In the view illustrated in FIG. 13C, the collector 1202 is fully inserted and attached to the housing 1204.

Figure 14A:
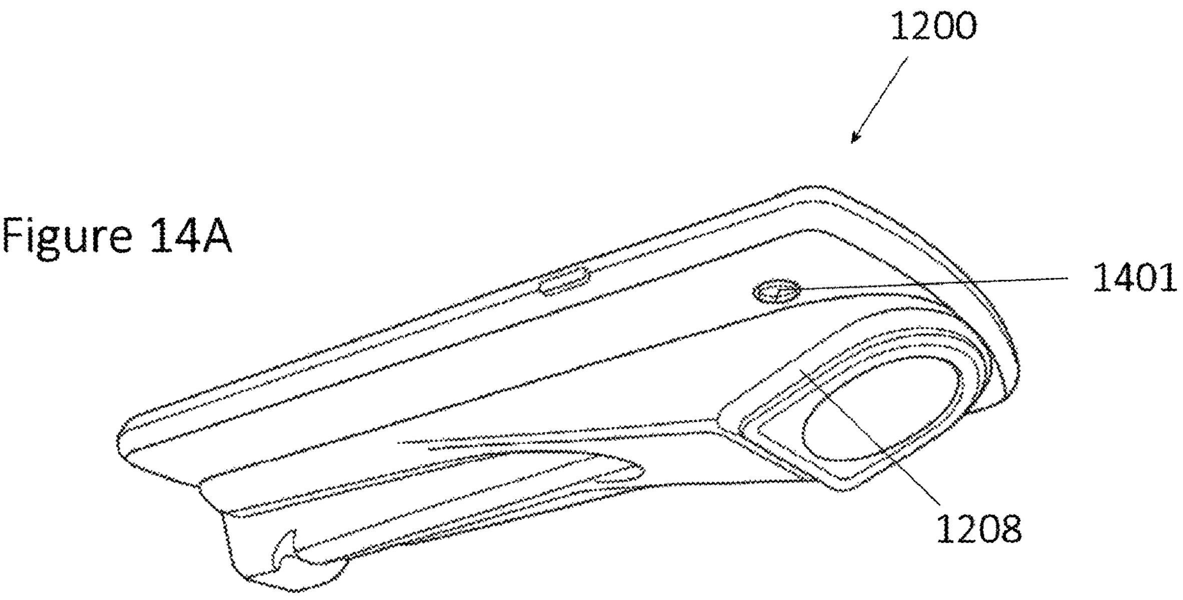
FIG. 14A illustrates a bottom perspective view of the collection device of FIG. 12 having the collector disposed in a first position.

FIG. 14A shows the underside of the collection device 1200. In this embodiment, the smartphone's camera 1401 can read the barcode 1208 on the collector 1202. Since each collector 1202 has a unique identifier, the device 1200 will be able to match the specific collector to the time and location of sampling.

Figure 14B:
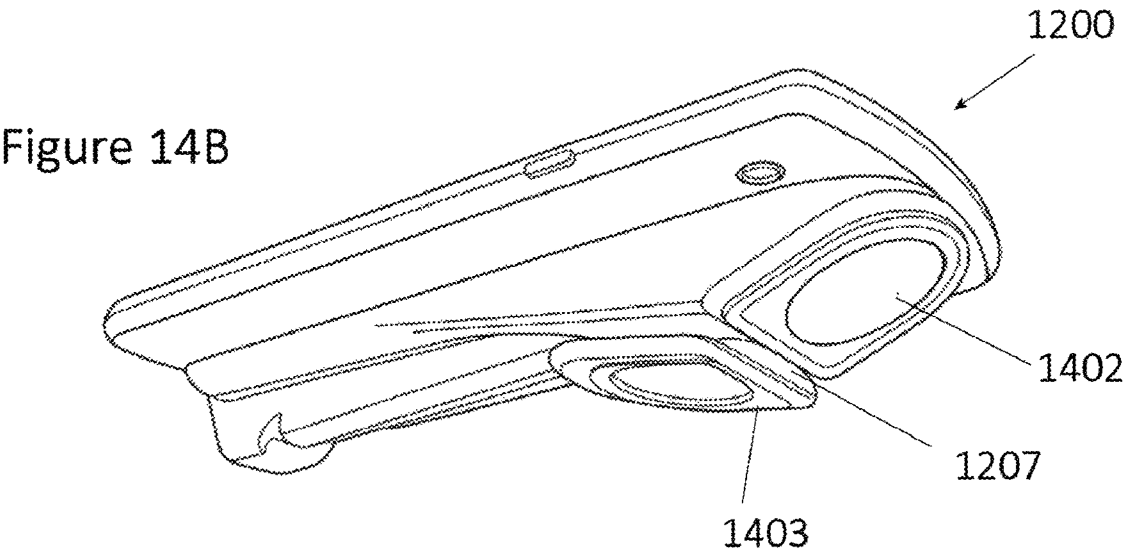
FIG. 14B illustrates a bottom perspective view of the collection device of FIG. 12 having the collector disposed in a second position.

As illustrated in FIG. 14B, the collector body 1202 has been opened at the hinge 1207 to expose the swab surface 1402. A seal 1403 may be incorporated into the collector body 1204 to keep air and moisture away from the swab both prior to and after sampling and insure that any pathogens within the sample are captured. In one embodiment, the camera retains visibility of part of the collector when it is open. In this manner, the device insures that the collector is not only open and ready for sampling, but is still present.

The material of the swab 1402 may be chosen depending upon the specific pathogen being tested. Commonly used materials are cotton, PET and polyester. The collection device 1202 may also contain a neutralizing broth additive that neutralizes residual sanitizers that may be present on a surface. Swab materials and additives are well known in the art and will not be discussed in detail. In some embodiments, one collection device 1200 may be used to test for different pathogens, depending on the type of growth media used in processing the collected sample. One sample may also be used to test for multiple pathogens by splitting the sample between growth media. Additionally, a control sample may be contained within the collection device 1200. This can be an inert version of the pathogen being tested. There may be collection devices 1200 of differing types with materials and additives selected for specific pathogens of interest. The collection device 1202 to be used may be chosen by the type of pathogen being studied. Since all collection devices 1200 are individually identified, the device can determine whether the correct collector is being used.

Figure 15:
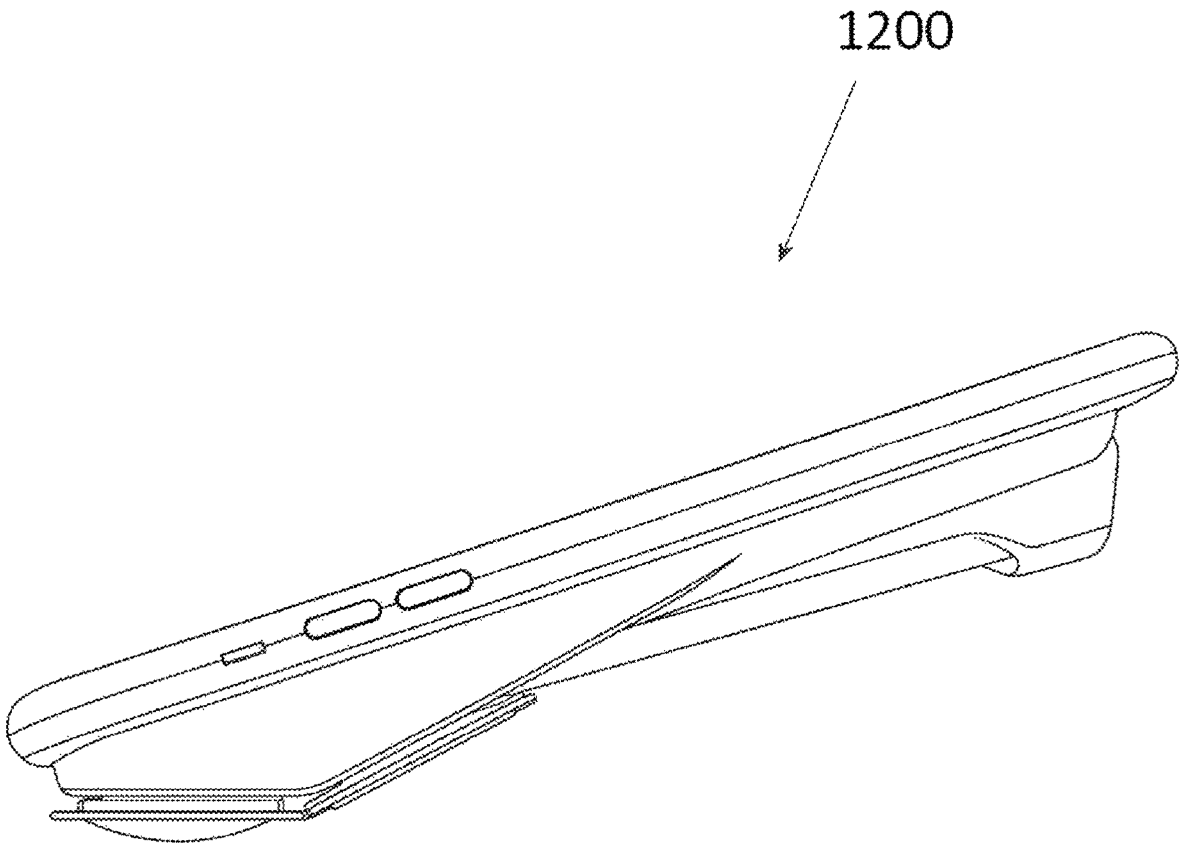
FIG. 15 illustrates the collection device of FIG. 12 in position ready to sample a horizontal surface.
Figure 16:
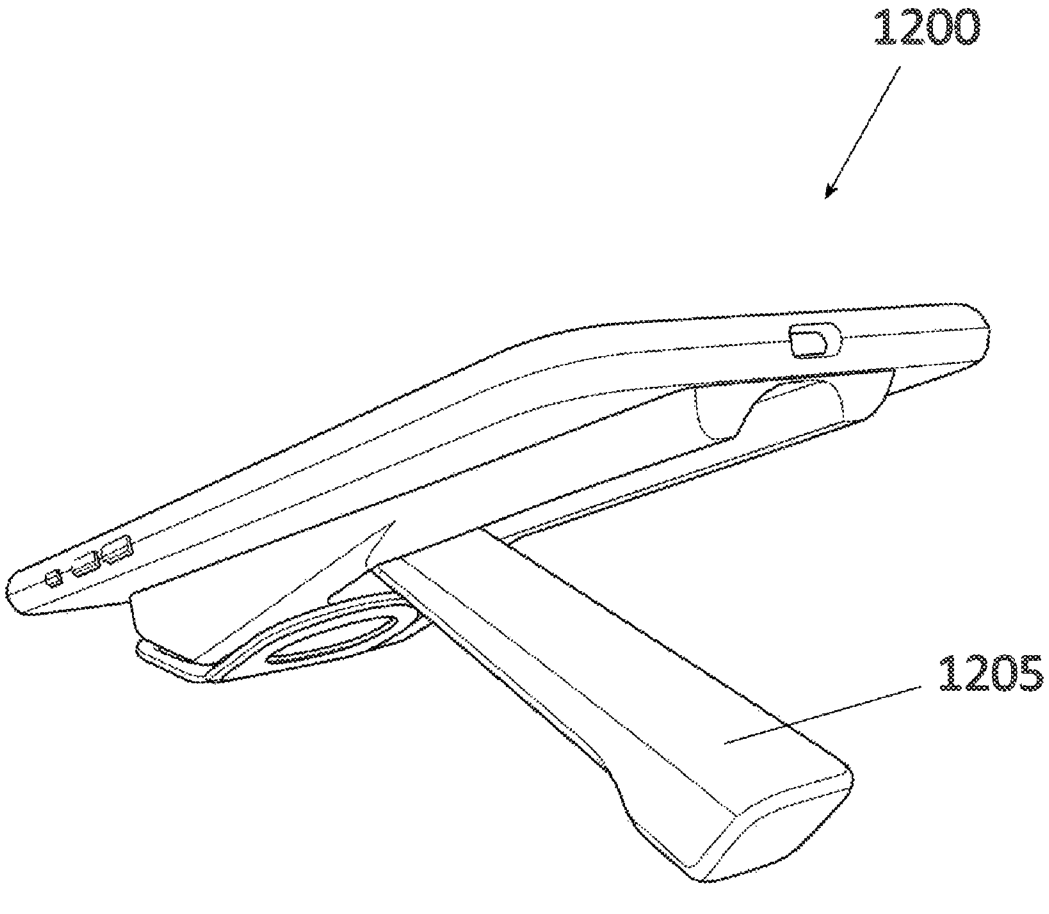
FIG. 16 illustrates the collection device of FIG. 12 with a retractable handle disposed in a lowered state.

FIG. 15 shows the collection device 1200 in position ready to sample a horizontal surface. FIG. 16 shows an embodiment of the collection device 1200 with a retractable handle 1200 that is lowered to allow a user to grasp and maneuver the collection device 1200 during a sample collection procedure.

The collection device 1200 performs many functions that aid in accurate and consistent sampling. In one scenario of its use, the technician turns on the device and logs on to the detection and display system 10. This may be a manual login, but is preferably an automatic recognition of the technician. This can be accomplished in ways that include scanning a bar code, QR code or other identifier that is on the technician's identification badge. Many user devices are configured with the ability to read finger or thumb prints, or perform retina scans. This offers a positive identification of the person using the device.

Once logged onto the detection and display system 10, the collection device 1200 receives sampling instructions from the pathogen display system's controller. The sampling device can now pass these instructions to the user through the audio and video capabilities of the device's smartphone. Instructions may include which room or area will be sampled, where within the area to sample, which collection device 1202 to use, when a sample has been correctly taken and other information. The scenario may go as follows:

The technician turns on the collection device 18 and logs into the detection and display system 10 via thumbprint scan, etc.

The technician is instructed by the control system 18 to go to a particular space within the facility.

The technician is instructed by the control system 18 to attach a collector 1202 to the device 1200. In cases where there is more than one type of collector available, the type will be specified. The device 1200 identifies the collector as being an unused collector of the correct type, and records the identifier.

The technician is instructed by the control system 18 to open the collector, exposing the swab portion. The device confirms that the collector is ready to swab.

The technician is instructed by the control system 18 to take a sample from a specified location. In some embodiments, the device utilizes the smartphone's onboard GPS, accelerometer and orientation capabilities. By using these capabilities, the control system 18 can determine the exact location of the sample, the velocity at which the sample was taken and the angle of the device in two axes.

Some embodiments may include a force measurement. This can be accomplished by including a force sensor in the device housing and transmitting the data to the smartphone. Alternatively, certain smartphones are configured with pressure sensitive displays, the onboard sensor may be used. The technician can be instructed to hold the device and press on a location on the display to apply pressure to the swab. The pressure on the display can be used to calculate the actual force on the swab.

With this information, the device 1200 can assure that the sample was taken at the correct location and sampling area, that the swab passed over the surface at the optimal sampling velocity, that the angle corresponds to the orientation of the surface being sampled, and that the optimal amount of force was put on the swab. If any of these sensed sampling parameters are not optimal, the device can give the technician instructions to correct their technique. The device may even give the technician a score on their performance, for example 1-10, for immediate feedback on the quality of their sampling technique.

Once a sample is complete, the device 1200 can instruct the technician to close the collector 1202 and remove it from the device 1200. It may also instruct the technician as to what to do with the used collector.

The sample is now complete. The device can instruct the technicians to take another sample within the area, move to a new area, etc.

Reading System

Some embodiments of the innovation may include a system that samples and cultures potentially harmful microbes within a health care environment, and identifies and categorizes pathogens. This uses a method that automates certain culturing operations and methods, as described above, and manages others to create a complete solution for the detection and classification of harmful pathogens.

Bacteria, spores, etc. that are collected during the sampling process are microscopic. In order to facilitate visual recognition, they are allowed to grow into a colony. This is accomplished by placing the sample into a growth medium such as agar or nutrient broth, then incubating at an elevated temperature to promote growth. In general, visible growth occurs within six hours, although it can take up to 48 hours to positively identify a microorganism and its strain. The particular growth media will be selected based on the types of pathogens of interest, e.g. MRSA, C.diff, *acinetobacter*, etc. In some embodiments, more than one growth medium may be used, and the sample tested for multiple pathogens.

An imaging camera can be used to monitor and survey sample growth over time. Images of the samples may be captured and stored over time. This camera may be visible-light, infrared or a combination. The type of camera used will depend on the specific pathogens of interest and at what wavelength of light they are most easily visible.

An objective lens may be used to focus the image of the growing culture. This may be a stationary fixed-focus lens, or may comprise an adjustable focus. If an adjustable focus lens is included, it can be used to measure the height of growth of the colony (by focusing top and bottom of the colony and measuring distance) if this information is deemed useful in identifying a pathogen.

Illumination of the sample may also be selective. For example, if a particular pathogen reflects one wavelength of light better than another, a light source that produces that wavelength may be used. The preferable light source is one or an array of LEDs, since they are available to produce a variety of colors. An array may be used to produce a multiple of specific wavelengths that can be used singularly or in combination to facilitate the visualization of multiple pathogens.

The system includes a computerized device, such as a computer system having a controller such as a memory and a processor, to identify potentially harmful pathogens. As microbe colonies grow, they develop with recognizable patterns. These patterns can be used to identify the microbes. The computer system contains a database comprising images of all microbes of interest. This database can be modified as new species of microbes emerge. The computerized device is configured to compare the image captured by the camera to images in the database and determines matches. The camera and computer are configured to automatically perform the same function that a morphologist performs when manually testing samples. The current innovation has the advantage of automation, infrared imaging, adaptive lighting and a nearly infinite library of pathogens and other organisms. The library may contain images of pathogens at varying stages of their growth to aid in early identification. The library may also contain non-pathogenic microbe images that may be used to eliminate samples that are not of interest.

The computerized device is configured to compare the visible image to the database and looks for matching patterns. In samples with active microorganisms, growth should start to be visible within approximately six hours. If after six hours there is no growth, then there are no microorganisms within the sample. The computerized device can then stop the comparison and save the results as a no growth culture. This is done on an ongoing basis until the pattern is developed enough to make a positive or negative identification. Once a microbe has been identified, the results are reported. The computerized device is also configured to measure the size of the colony. The size may be measured as square area or cubic volume and mass may be calculated from the volume. In this manner, the system has the ability to determine both the type and colony size of the pathogen.

Once the microbes that have been identified are analyzed and classified by the computerized device, the results can be reported as:

No growth: if no growth is seen within the prescribed time, no microbes are present.

Growth not of interest: microbial growth is present, but the microbes are not harmful.

Harmful pathogen: microbes are present, and are deemed to be harmful pathogens.

Results uncertain: growth is present, but a positive identification could not be made.

The control system 18 is configured to learn as test results are obtained in order to accelerate the identification process. Images are obtained throughout the growth process, and the system can look for similarities in growth patterns. Early tests may take 24 to 48 hours to return a positive identification. However, growth of a particular microbe may follow a unique pattern that allows the system to recognize it prior to it being developed enough for a visual recognition. Primary observations may be made by the system such as color, shape, size, growth rate, luminescence, etc., as well as more subtle observations such as rate of change of the primary observations. The ability to recognize a particular pattern of growth prior to the development of an identifiable growth will allow identification to be made earlier in the growth process. This automated system will have the ability to recognize multiple patterns during the growth process, allowing identification of multiple microbes in a sample.

FIG. 18 shows a schematic representation of the components within a reading system 1800. The reading system 1800 includes a camera 1801, such as the imaging camera described above. This may be a visible light or infrared camera 1801, or a combination camera. While a single camera 1801 is illustrated, the reading system 1800 can include multiple cameras. These may be fixed or variable focus, depending on the detail of readings desired.

The reading system 1800 can include a lighting device 1802 configured to project single or multiple light frequencies, and may one, two or an array of lights. A holding device 1803 holds collectors containing samples to be determined. In some embodiments, the holder device 1803 holds multiple collectors, for example, in a carousel device. If a carousel device is used, the reading system 1800 can include a turntable 1804. The reading system 1800 also includes a computerized device (not shown) having a controller such as a processor and a memory or other suitable control device. The controller is configured to operate the cameras and lights, as well as the turntable and any other devices that are part of the reader, contains software that compares and determines pathogen content, and communicates with the pathogen display system's control system. It also has access to the pathogen database. The reading system 1800 may have a stand-alone control system, or may share part or all of its functions with the pathogen display system's control system.

Figure 19:
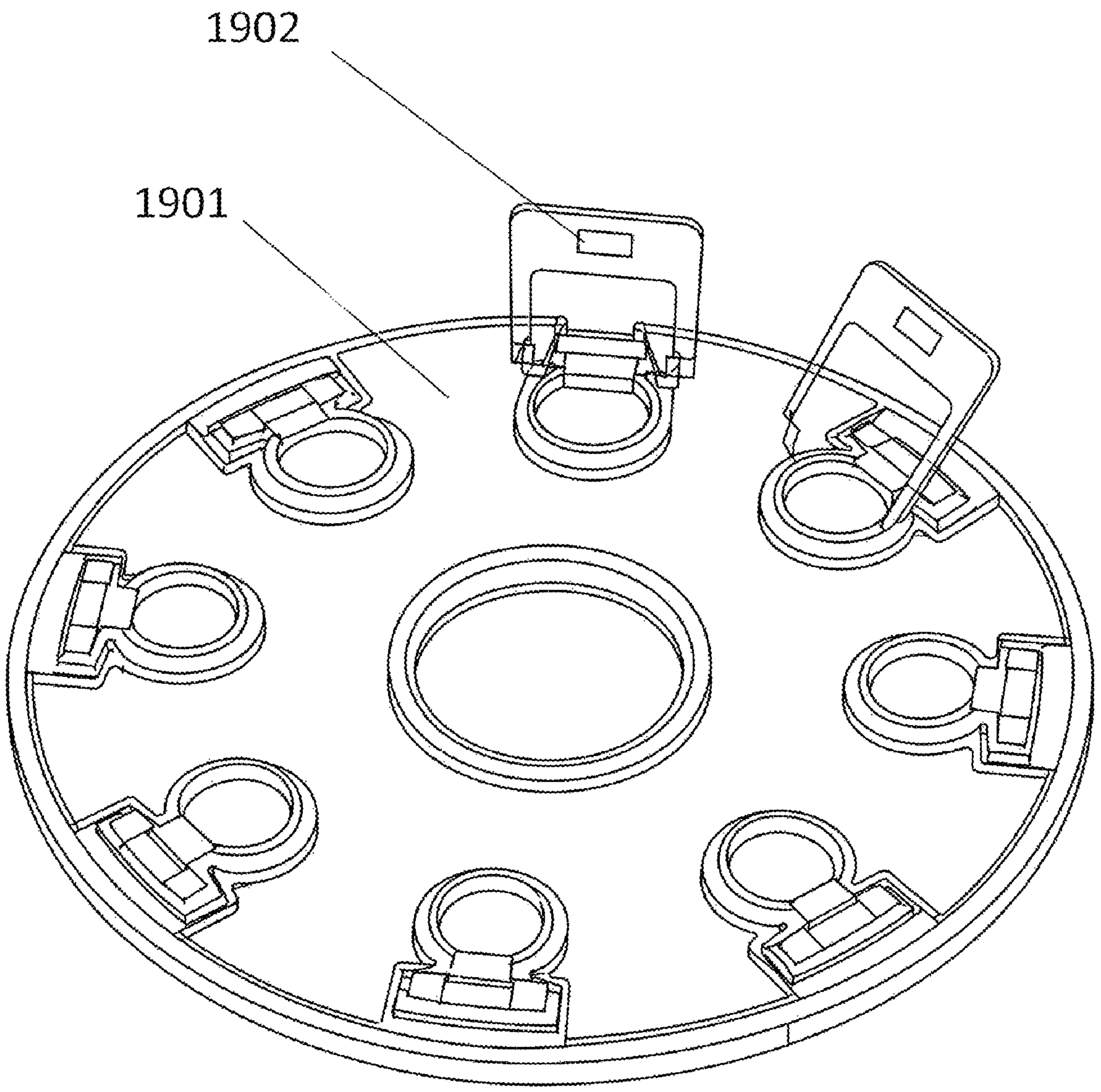
FIG. 19 illustrates a carousel, according to one arrangement.

FIG. 19 shows an example of the carousel device 1901. A collector 1902 is disposed within the carousel device 1901. The carousel device 1901 shown has space for 8 samples. A carousel device 1901 may have more or less spaces as determined by design intent. A reading system 1800 may be able to accept multiple carousels and include an indexing means. Alternatively, the reader system 1800 may use mechanisms other than a carousel device 1901 to hold one or multiple collectors.

In use, the reading system 1800 is configured to move a selected collector 1902 into position to be viewed by the camera 1801. The reading system 1800 can read the identifier on the collector 1902, which will correlate it to the sample location and time. This minimizes or eliminates the possibility of intermixing samples and producing incorrect results. Since each collector's results take several hours, the reader can cycle each collector into view in an intermittent fashion. As each sample reaches the point at which a determination is made, the result is logged and may be displayed. In some embodiments, the reader includes a mechanism that removes a collector that has been completed and replaces it with another untested one.

Certification

Figure 20:
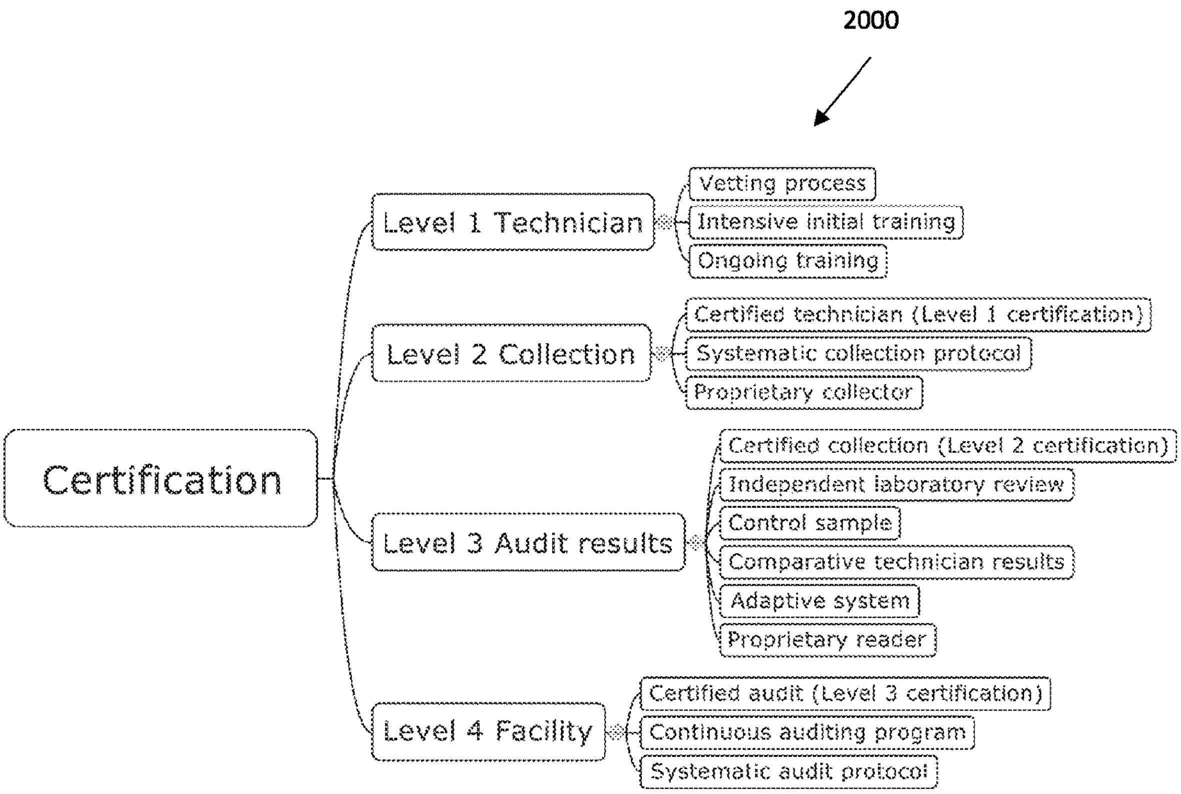
FIG. 20 illustrates certification levels of a pathogen auditing program.

The systems, methods and apparatus described herein may be used a means to certify a pathogen auditing program. This certification may be considered on four levels. The flowchart 2000 in FIG. 20 illustrates these certification levels.

Level 1 certifies the technician. This assures that the collection techniques used by all technicians are correct and consistent. This begins with a vetting process for each technician to confirm that they have the necessary skills and abilities to understand and carry out successful collections. The specific skills required will be determined with practice of the art. All technicians will undergo intensive initial training, as well as ongoing training, to certify them in the proper use of devices, testing methods and protocols, as well as ethical and performance standards.

Level 2 certifies the collection of samples. This certification level assures that samples are taken in the specified locations, at the specified times, using the correct methods and techniques. This begins with technicians that are certified at Level 1. The system presents a set of collection instructions to the technicians who are proficient at collection techniques, protocols, etc. These collection locations and methods have been determined by the system to be the most likely to find pathogen contamination. The proprietary collector adds another layer of assurance to the certification. The collector recognizes the technician and monitors their movements, sampling location and sampling technique. If samples are not collected as expected by the system, it can instantly instruct the technician with corrections. This aids in removing human error from the system.

Level 3 certifies the audit results. This begins with the Level 2 certified collections. An independent laboratory review adds another layer of certainty to the results, as does the control sample as described above. Comparing results between technicians adds one more layer of control. Technicians whose results vary from the norm can be reviewed to understand the differences and actions may be taken to bring them into compliance. As an adaptive system, sampling instructions are constantly being reviewed and revised based on historical results in an effort to create a constantly improving result. Embodiments that utilize the proprietary reader add an additional level of confidence. As with the collector, this device aids in removing human error as a factor in determining pathogen content.

Level 4 certifies the facility. At this level, entire facilities, or select units within a facility, enroll in a continuous auditing program. The nature of pathogen spread and growth is unpredictable and changeable. It is important that Level 3 audits are conducted in an ongoing manner to truly understand the circumstance of pathogens within a facility. The data produced by these audits has a cumulative learning effect on the adaptive systematic audit protocols that are created by the system. This certification can be enhanced as multiple facilities join the system and share.

While various embodiments of the innovation have been particularly shown and described, it will be understood by those skilled in the art that various changes in form and details may be made therein without departing from the spirit and scope of the innovation as defined by the appended claims.

What is claimed is:

1. In a control system of a detection and display system, a method of identifying predicted pathogen contamination, comprising:

receiving, by the control system, pathogen sample information identifying a size of a pathogen colony associated with an environmental surface of a first location of a facility;

correlating, by the control system, the pathogen sample information with a set of pathogen transmission factors, each pathogen transmission factor of the set of pathogen transmission factors associated with transmission of the pathogen within the facility;

executing, by the control system, a discriminant analysis based upon the set of pathogen transmission factors to predict pathogen contamination at an environmental surface of a subsequent location of the facility based upon the pathogen sample information;

displaying, by the control system, a graphical representation of a map of the facility on an output device; and highlighting on the graphical representation of the map of the facility, by the control system, the first location with a first color and the subsequent location having the predicted pathogen contamination and the predicted pathogen contamination at the environmental surface of the subsequent location with a second color indicative of pathogen contamination.

2. The method of claim 1, wherein the pathogen sample information is configured as at least one of a pathogen sample type, a pathogen sample collection time, and a pathogen sample collection location.

3. The method of claim 1, wherein a pathogen transmission factor of the set of pathogen transmission factors is configured as a patient perimeter associated with a patient location within the facility.

4. The method of claim 3, wherein executing the discriminant analysis based upon the set of pathogen transmission factors to predict pathogen contamination at the environmental surface of the subsequent location of the facility based upon the pathogen sample information comprises executing, by the control system, the discriminant analysis based upon the set of pathogen transmission factors to predict pathogen contamination at the environmental surface of the subsequent location of the facility based upon the pathogen sample information and the patient perimeter associated with the patient location within the facility.

5. The method of claim 1, wherein the size of the pathogen colony comprises at least one of an area of the pathogen colony, a volume of the pathogen colony, a mass of the pathogen colony, and a percentage of the environmental surfaces contaminated with pathogen.

6. The method of claim 1, wherein a pathogen transmission factor of the set of pathogen transmission factors is configured as a volume of traffic entering the first location of the facility.

7. The method of claim 6, wherein the volume of traffic entering the first location of the facility comprises a volume of human traffic entering the first location of the facility.

8. The method of claim 6, wherein the volume of traffic entering the first location of the facility comprises a volume of equipment traffic entering the first location of the facility.

9. A pathogen detection and display system, comprising:

a collection device configured to retrieve a sample from a facility;

a reading device configured to receive the sample from the collection device, to process the sample, and to generate pathogen sample information related to the sample;

a control system disposed in electrical communication with the reading device; and an output device disposed in electrical communication with the control system;

wherein the control system is configured to:

receive pathogen sample information identifying a size of a pathogen colony associated with an environmental surface of a first location of a facility;

correlate the pathogen sample information with a set of pathogen transmission factors, each pathogen transmission factor of the set of pathogen transmission factors associated with transmission of the pathogen within the facility;

execute a discriminant analysis based upon the set of pathogen transmission factors to predict pathogen contamination at an environmental surface of a subsequent location of the facility based upon the pathogen sample information;

display a graphical representation of a map of the facility on the output device; and highlight on the graphical representation of the map of the facility the first location with a first color and the subsequent location having the predicted pathogen contamination, and the predicted pathogen contamination at the environmental surface of the subsequent location with a second color indicative of pathogen contamination.

10. The pathogen detection and display system of claim 9, wherein the pathogen sample information is configured as at least one of a pathogen sample type, a pathogen sample collection time, and a pathogen sample collection location.

11. The pathogen detection and display system of claim 9, wherein a pathogen transmission factor of the set of pathogen transmission factors is configured as a patient perimeter associated with a patient location within the facility.

12. The pathogen detection and display system of claim 11, wherein when executing the discriminant analysis based upon the set of pathogen transmission factors to predict pathogen contamination at the environmental surface of the subsequent location of the facility based upon the pathogen sample information, the control system is configured to execute the discriminant analysis based upon the set of pathogen transmission factors to predict pathogen contamination at the environmental surface of the subsequent location of the facility based upon the pathogen sample information and the patient perimeter associated with the patient location within the facility.

13. The pathogen detection and display system of claim 6, wherein the size of the pathogen colony comprises at least one of an area of the pathogen colony, a volume of the pathogen colony, a mass of the pathogen colony, and a percentage of the environmental surfaces contaminated with pathogen.

14. The pathogen detection and display system of claim 6, wherein a pathogen transmission factor of the set of pathogen transmission factors is configured as a volume of traffic entering the first location of the facility.

15. The pathogen detection and display system of claim 14, wherein the volume of traffic entering the first location of the facility comprises a volume of human traffic entering the first location of the facility.

16. The pathogen detection and display system of claim 14, wherein the volume of traffic entering the first location of the facility comprises a volume of equipment traffic entering the first location of the facility.

* * * * *